(12) United States Patent
Lenker et al.

(10) Patent No.: US 8,597,277 B2
(45) Date of Patent: Dec. 3, 2013

(54) EXPANDABLE TRANSLUMINAL SHEATH

(75) Inventors: Jay Lenker, Laguna Beach, CA (US);
Onnik Tchulluian, Carlsbad, CA (US);
Edward J. Nance, Corona, CA (US)

(73) Assignee: Onset Medical Corporation, Irvine, CA (US)

( * ) Notice: Subject to any disclaimer, the term of this patent is extended or adjusted under 35 U.S.C. 154(b) by 0 days.

(21) Appl. No.: 13/046,519

(22) Filed: Mar. 11, 2011

(65) Prior Publication Data

US 2011/0282156 A1 Nov. 17, 2011

Related U.S. Application Data

(63) Continuation of application No. 11/223,897, filed on Sep. 9, 2005, now abandoned.

(60) Provisional application No. 60/608,355, filed on Sep. 9, 2004.

(51) Int. Cl.
*A61M 25/16* (2006.01)

(52) U.S. Cl.
USPC ....... 604/533; 264/301; 427/2.1; 604/103.09; 604/104; 604/106; 604/264; 604/524; 604/508; 604/509; 604/239; 604/272; 604/107; 606/194; 606/198; 600/208

(58) Field of Classification Search
USPC ............... 264/301; 427/2.1; 604/103.09, 104, 604/106, 264, 524, 508, 509, 239, 272, 604/107; 606/194, 198; 600/208
See application file for complete search history.

(56) References Cited

U.S. PATENT DOCUMENTS

| | | | |
|---|---|---|---|
| 319,296 A * | 6/1885 | Molesworth | 606/198 |
| 668,879 A | 2/1901 | Miller | |
| 1,213,001 A | 1/1917 | Philips | |
| 1,248,492 A | 12/1917 | Hill | |
| 2,042,900 A | 6/1936 | James | |
| 2,548,602 A | 4/1948 | Greenburg | |
| 3,509,883 A | 5/1970 | Dibelius | |

(Continued)

FOREIGN PATENT DOCUMENTS

| | | |
|---|---|---|
| EP | 0 177 177 | 4/1986 |
| EP | 0 249 456 | 12/1987 |

(Continued)

OTHER PUBLICATIONS

Jan. 8, 2007 Non/final rejection in U.S. Appl. No. 11/415,764, filed May 2, 2006.

(Continued)

*Primary Examiner* — Nicholas Lucchesi
*Assistant Examiner* — Scott Medway
(74) *Attorney, Agent, or Firm* — Knobbe, Martens, Olson & Bear LLP

(57) ABSTRACT

Disclosed is an expandable transluminal sheath, for introduction into the body while in a first, low cross-sectional area configuration, and subsequent expansion of at least a part of the distal end of the sheath to a second, enlarged cross-sectional configuration. The distal end of the sheath is maintained in the first, low cross-sectional configuration and expanded using a radial dilatation device. In an exemplary application, the sheath is utilized to provide access for diagnostic or therapeutic procedures such as ureteroscopy, cardiac electrophysiology, gastroenterology, and spinal access.

5 Claims, 17 Drawing Sheets

(56) References Cited

U.S. PATENT DOCUMENTS

| | | | |
|---|---|---|---|
| 3,545,443 A | 12/1970 | Ansari | |
| 3,742,958 A | 7/1973 | Rundles | |
| 3,789,852 A | 2/1974 | Kim et al. | |
| 3,902,492 A | 9/1975 | Greenhalgh | |
| 4,018,230 A | 4/1977 | Ochiai et al. | |
| 4,141,364 A | 2/1979 | Schultze | |
| 4,401,433 A | 8/1983 | Luther | |
| 4,411,655 A | 10/1983 | Schreck | |
| 4,451,256 A | 5/1984 | Weikl et al. | |
| 4,479,497 A | 10/1984 | Fogarty et al. | |
| 4,581,025 A | 4/1986 | Timmermans | |
| 4,589,868 A | 5/1986 | Dretler | |
| 4,601,713 A | 7/1986 | Fuqua | |
| 4,610,688 A | 9/1986 | Silvestrini et al. | |
| 4,636,346 A | 1/1987 | Gold et al. | |
| 4,650,466 A | 3/1987 | Luther | |
| 4,710,181 A | 12/1987 | Fuqua | |
| 4,716,901 A | 1/1988 | Jackson et al. | |
| 4,738,666 A | 4/1988 | Fuqua | |
| 4,739,762 A | 4/1988 | Palmaz | |
| 4,772,266 A | 9/1988 | Groshong | |
| 4,790,817 A | 12/1988 | Luther | |
| 4,798,193 A | 1/1989 | Giesy et al. | |
| 4,846,791 A | 7/1989 | Hattler et al. | |
| 4,865,593 A | 9/1989 | Ogawa et al. | |
| 4,869,717 A | 9/1989 | Adair | |
| 4,884,573 A * | 12/1989 | Wijay et al. | 606/194 |
| 4,888,000 A | 12/1989 | McQuilkin et al. | |
| 4,896,669 A | 1/1990 | Bhate et al. | |
| 4,898,591 A * | 2/1990 | Jang et al. | 604/527 |
| 4,899,729 A | 2/1990 | Gill et al. | |
| 4,921,479 A | 5/1990 | Grayzel | |
| 4,954,126 A | 9/1990 | Wallsten | |
| 4,955,895 A | 9/1990 | Sugiyama et al. | |
| 4,972,827 A | 11/1990 | Kishi et al. | |
| 4,984,564 A | 1/1991 | Yuen | |
| 4,986,830 A | 1/1991 | Owens et al. | |
| 5,011,488 A | 4/1991 | Ginsburg et al. | |
| 5,035,686 A | 7/1991 | Crittenden et al. | |
| 5,045,056 A | 9/1991 | Behl | |
| 5,057,092 A * | 10/1991 | Webster, Jr. | 604/527 |
| 5,059,183 A | 10/1991 | Semrad | |
| 5,066,285 A * | 11/1991 | Hillstead | 604/164.01 |
| 5,073,166 A | 12/1991 | Parks et al. | |
| 5,078,736 A | 1/1992 | Behl | |
| 5,092,839 A | 3/1992 | Kipperman | |
| 5,098,393 A * | 3/1992 | Amplatz et al. | 604/167.03 |
| 5,100,388 A | 3/1992 | Behl et al. | |
| 5,108,413 A | 4/1992 | Moyers | |
| 5,108,416 A | 4/1992 | Ryan et al. | |
| 5,112,304 A | 5/1992 | Barlow et al. | |
| 5,112,308 A | 5/1992 | Olsen et al. | |
| 5,116,318 A | 5/1992 | Hillstead | |
| 5,122,122 A | 6/1992 | Allgood | |
| 5,139,511 A | 8/1992 | Gill et al. | |
| 5,147,316 A | 9/1992 | Castillenti | |
| 5,158,545 A | 10/1992 | Trudell et al. | |
| 5,163,903 A | 11/1992 | Crittenden et al. | |
| 5,176,659 A | 1/1993 | Mancini | |
| 5,183,464 A | 2/1993 | Dubrul et al. | |
| 5,188,602 A | 2/1993 | Nichols | |
| 5,201,756 A | 4/1993 | Horzewski et al. | |
| 5,222,938 A | 6/1993 | Behl | |
| 5,222,971 A | 6/1993 | Willard et al. | |
| 5,234,425 A | 8/1993 | Fogarty et al. | |
| 5,250,025 A | 10/1993 | Sosnowski et al. | |
| 5,250,033 A | 10/1993 | Evans et al. | |
| 5,256,150 A | 10/1993 | Quiachon et al. | |
| 5,275,611 A | 1/1994 | Behl | |
| 5,279,553 A | 1/1994 | Winkler et al. | |
| 5,295,994 A | 3/1994 | Bonutti | |
| 5,312,360 A | 5/1994 | Behl | |
| 5,312,417 A * | 5/1994 | Wilk | 606/114 |
| 5,316,360 A | 5/1994 | Feikma | |
| 5,318,588 A | 6/1994 | Horzewski et al. | |
| 5,320,611 A | 6/1994 | Bonutti et al. | |
| 5,324,261 A | 6/1994 | Amundson et al. | |
| 5,346,503 A | 9/1994 | Chow et al. | |
| 5,380,304 A | 1/1995 | Parker | |
| 5,392,766 A | 2/1995 | Masterson et al. | |
| 5,395,341 A | 3/1995 | Slater | |
| 5,395,349 A | 3/1995 | Quiachon et al. | |
| 5,407,430 A | 4/1995 | Peters | |
| 5,409,469 A | 4/1995 | Schaerf | |
| 5,431,676 A | 7/1995 | Dubrul et al. | |
| 5,433,708 A | 7/1995 | Nichols et al. | |
| 5,447,503 A * | 9/1995 | Miller | 604/528 |
| 5,454,788 A * | 10/1995 | Walker et al. | 604/99.04 |
| 5,454,790 A | 10/1995 | Dubrul | |
| 5,460,170 A | 10/1995 | Hammerslag | |
| 5,507,767 A | 4/1996 | Maeda et al. | |
| 5,514,091 A | 5/1996 | Yoon | |
| 5,514,236 A | 5/1996 | Avellanet et al. | |
| 5,527,336 A | 6/1996 | Rosenbluth et al. | |
| 5,531,721 A * | 7/1996 | Pepin et al. | 604/525 |
| 5,540,658 A | 7/1996 | Evans et al. | |
| 5,542,928 A | 8/1996 | Evans et al. | |
| 5,549,635 A | 8/1996 | Solar | |
| 5,571,089 A | 11/1996 | Crocker | |
| 5,573,509 A | 11/1996 | Thornton | |
| 5,573,517 A | 11/1996 | Bonutti et al. | |
| 5,573,520 A * | 11/1996 | Schwartz et al. | 604/526 |
| 5,657,963 A * | 8/1997 | Hinchliffe et al. | 251/149.1 |
| 5,662,614 A | 9/1997 | Edoga | |
| 5,672,158 A | 9/1997 | Okada et al. | |
| 5,674,240 A | 10/1997 | Bonutti et al. | |
| 5,674,590 A | 10/1997 | Anderson et al. | |
| 5,700,253 A | 12/1997 | Parker | |
| 5,702,373 A | 12/1997 | Samson | |
| 5,709,713 A * | 1/1998 | Evans et al. | 623/1.53 |
| 5,713,867 A | 2/1998 | Morris | |
| 5,738,667 A | 4/1998 | Solar | |
| 5,766,203 A | 6/1998 | Imran et al. | |
| 5,776,141 A | 7/1998 | Klein et al. | |
| 5,810,776 A | 9/1998 | Bacich et al. | |
| 5,817,100 A | 10/1998 | Igaki | |
| 5,846,251 A | 12/1998 | Hart | |
| 5,868,719 A | 2/1999 | Tsukernik | |
| 5,868,779 A | 2/1999 | Ruiz | |
| 5,885,217 A | 3/1999 | Gisselberg et al. | |
| 5,888,196 A | 3/1999 | Bonutti | |
| 5,902,282 A | 5/1999 | Balbierz | |
| 5,908,435 A * | 6/1999 | Samuels | 606/200 |
| 5,916,145 A | 6/1999 | Chu et al. | |
| 5,922,019 A | 7/1999 | Hankh et al. | |
| 5,944,691 A * | 8/1999 | Querns et al. | 604/104 |
| 5,961,499 A | 10/1999 | Bonutti et al. | |
| 5,964,730 A | 10/1999 | Williams et al. | |
| 5,971,938 A | 10/1999 | Hart et al. | |
| 5,997,508 A | 12/1999 | Lunn et al. | |
| 6,030,364 A | 2/2000 | Durgin et al. | |
| 6,056,718 A * | 5/2000 | Funderburk et al. | 604/93.01 |
| 6,063,056 A * | 5/2000 | Engelberg | 604/97.01 |
| 6,080,174 A | 6/2000 | Dubrul et al. | |
| 6,090,072 A | 7/2000 | Kratoska et al. | |
| 6,120,480 A | 9/2000 | Zhang et al. | |
| 6,123,689 A | 9/2000 | To et al. | |
| 6,168,579 B1 | 1/2001 | Tsugita | |
| 6,183,443 B1 | 2/2001 | Kratoska et al. | |
| 6,187,000 B1 | 2/2001 | Davison et al. | |
| 6,197,016 B1 | 3/2001 | Fourkas et al. | |
| 6,228,052 B1 | 5/2001 | Pohndorf | |
| 6,248,116 B1 * | 6/2001 | Chevillon et al. | 606/139 |
| 6,280,452 B1 | 8/2001 | Mears | |
| 6,293,909 B1 | 9/2001 | Chu et al. | |
| 6,312,443 B1 | 11/2001 | Stone | |
| 6,443,979 B1 | 9/2002 | Stalker et al. | |
| 6,447,540 B1 | 9/2002 | Fontaine et al. | |
| 6,471,684 B2 | 10/2002 | Dulak et al. | |
| 6,494,860 B2 | 12/2002 | Rocamora et al. | |
| 6,494,893 B2 | 12/2002 | Dubrul et al. | |
| 6,517,551 B1 * | 2/2003 | Driskill | 606/113 |
| 6,524,268 B2 | 2/2003 | Hayner et al. | |
| 6,524,320 B2 | 2/2003 | DiPoto | |

(56) References Cited

U.S. PATENT DOCUMENTS

| | | | |
|---|---|---|---|
| 6,530,902 | B1 | 3/2003 | Jonkman |
| 6,537,247 | B2 | 3/2003 | Shannon |
| 6,582,395 | B1 | 6/2003 | Burkett et al. |
| 6,613,038 | B2* | 9/2003 | Bonutti et al. ............... 604/509 |
| 6,613,062 | B1 | 9/2003 | Leckrone et al. |
| 6,616,678 | B2 | 9/2003 | Nishtala et al. |
| 6,638,268 | B2 | 10/2003 | Niazi |
| 6,679,902 | B1 | 1/2004 | Boyle et al. |
| 6,692,462 | B2 | 2/2004 | Mackenzie et al. |
| 6,692,482 | B2 | 2/2004 | Heller et al. |
| 6,706,017 | B1 | 3/2004 | Dulguerov |
| 6,808,520 | B1 | 10/2004 | Fourkas et al. |
| 6,827,683 | B2 | 12/2004 | Otawara |
| 6,951,555 | B1* | 10/2005 | Suresh et al. ............... 604/524 |
| 7,033,369 | B2 | 4/2006 | Davison et al. |
| 7,056,319 | B2 | 6/2006 | Aliperti et al. |
| 7,135,015 | B2 | 11/2006 | Dulak et al. |
| 7,285,109 | B2* | 10/2007 | Wu et al. ............... 604/103.03 |
| 7,309,334 | B2* | 12/2007 | von Hoffmann ............. 604/524 |
| 7,316,677 | B1 | 1/2008 | Dulak et al. |
| 7,329,268 | B2 | 2/2008 | Van Nguyen et al. |
| 7,449,011 | B2* | 11/2008 | Wenchell et al. ........ 604/164.01 |
| 7,457,661 | B2* | 11/2008 | Doty ............... 604/21 |
| 7,582,079 | B2* | 9/2009 | Wendlandt et al. ........... 604/525 |
| 7,694,681 | B2* | 4/2010 | Green ............... 128/207.14 |
| 7,914,512 | B2* | 3/2011 | Orth et al. ............... 604/506 |
| 2001/0012950 | A1 | 8/2001 | Nishtala et al. |
| 2001/0037126 | A1 | 11/2001 | Stack et al. |
| 2002/0009535 | A1 | 1/2002 | Michal et al. |
| 2002/0010440 | A1* | 1/2002 | Segesser ............... 604/272 |
| 2002/0010476 | A1 | 1/2002 | Mulholland et al. |
| 2002/0077653 | A1 | 6/2002 | Hudson et al. |
| 2002/0099258 | A1* | 7/2002 | Staskin et al. ............... 600/29 |
| 2002/0099431 | A1 | 7/2002 | Armstrong et al. |
| 2002/0161377 | A1 | 10/2002 | Rabkin |
| 2003/0050600 | A1 | 3/2003 | Ressemann et al. |
| 2003/0065353 | A1 | 4/2003 | Horzewski et al. |
| 2003/0135156 | A1 | 7/2003 | Bencini et al. |
| 2003/0195551 | A1 | 10/2003 | Davison et al. |
| 2003/0212384 | A1 | 11/2003 | Hayeden |
| 2003/0216770 | A1 | 11/2003 | Persidsky et al. |
| 2004/0006344 | A1 | 1/2004 | Nguyen et al. |
| 2004/0073286 | A1 | 4/2004 | Armstrong et al. |
| 2004/0087968 | A1 | 5/2004 | Core |
| 2004/0181273 | A1 | 9/2004 | Brasington et al. |
| 2004/0220549 | A1 | 11/2004 | Dittman et al. |
| 2004/0236346 | A1* | 11/2004 | Parker ............... 606/108 |
| 2005/0043780 | A1 | 2/2005 | Gifford et al. |
| 2005/0085842 | A1 | 4/2005 | Eversull et al. |
| 2005/0124937 | A1 | 6/2005 | Kick et al. |
| 2005/0125021 | A1 | 6/2005 | Nance et al. |
| 2005/0149105 | A1 | 7/2005 | Leeflang et al. |
| 2005/0222576 | A1 | 10/2005 | Kick et al. |
| 2005/0273149 | A1* | 12/2005 | Tran et al. ............... 623/1.11 |
| 2006/0036276 | A1 | 2/2006 | Nguyen et al. |
| 2006/0052750 | A1* | 3/2006 | Lenker et al. ............ 604/164.01 |
| 2006/0142795 | A1 | 6/2006 | Nguyen et al. |
| 2006/0200189 | A1 | 9/2006 | Nance et al. |
| 2006/0247602 | A1 | 11/2006 | Dulak et al. |
| 2007/0112335 | A1 | 5/2007 | Dulak et al. |

FOREIGN PATENT DOCUMENTS

| | | |
|---|---|---|
| EP | 0 385 920 | 9/1990 |
| EP | 0 206 553 | 1/1991 |
| EP | 0 421 650 | 4/1991 |
| EP | 0 546 766 | 6/1993 |
| WO | WO 92/19312 | 11/1992 |
| WO | WO 95/30374 | 11/1995 |
| WO | WO 99/16499 | 4/1999 |
| WO | WO 99/17665 | 4/1999 |
| WO | WO 03/090834 | 11/2003 |
| WO | WO2004/019760 | 3/2004 |

OTHER PUBLICATIONS

Jan. 15, 2009 Response to Jul. 14, 2008 European Patent Office Communication in European Application No. 05 794 899.4 filed on Sep. 8, 2005.
Jan. 18, 2008 Response to Oct. 18, 2007 non/final rejection in U.S. Appl. No. 10/728,728, filed Dec. 5, 2003.
Jan. 30, 2008 European Patent Office communication in European Application No. 04813043.9 filed on Mar. 12, 2004.
Feb. 19, 2009 Final rejection in U.S. Appl. No. 10/728,728, filed Dec. 5, 2003.
Mar. 8, 2010 European Office Action for application No. 05 794 916.6.
Mar. 19, 2010 Non/final rejection in U.S. Appl. No. 11/415,764, filed May 2, 2006.
May 1, 2007 Notice of allowance in U.S. Appl. No. 10/728,728, filed Dec. 5, 2003.
May 25, 2009 European Patent Office Communication in European Application No. 04813043.9 filed on Mar. 12, 2004.
Jun. 15, 2006 International Preliminary Report in International Application No. PCT/US2004/040651 filed on Dec. 3, 2004.
Jun. 30, 2009 Final rejection in U.S. Appl. No. 11/415,764, filed May 2, 2006.
Jul. 14, 2008 European Patent Office Communication in European Application No. 05 794 899.4 filed on Sep. 8, 2005.
Jul. 22, 2009 Non/final rejection in U.S. Appl. No. 11/415,659, filed May 2, 2006.
Jul. 23, 2009 Non/final rejection in U.S. Appl. No. 10/728,728, filed Dec. 5, 2003.
Aug. 3, 2010 Office Action for European Application No. 05 794 899.4 filed Sep. 8, 2005.
Aug. 11, 2008 Response to Jan. 30, 2008 European Patent Office Communication in European Application No. 04813043.9 on Mar. 12, 2004.
Aug. 13, 2009 European Office Action for application No. 05 794 916.6.
Aug. 13, 2009 European Office Action for application No. 05 794 899.4.
Sep. 13, 2006 non/final rejection in U.S. Appl. No. 10/728,728, filed Dec. 5, 2003.
Oct. 3, 2008 Non/final Rejection in U.S. Appl. No. 11/223,897, filed Sep. 9, 2005.
Oct. 16, 2009 Response to Apr. 17, 2009 Non/final rejection in U.S. Appl. No. 11/884,017, filed Jul. 2, 2004.
Oct. 18, 2007 Non/final rejection in U.S. Appl. No. 10/728,728, filed Dec. 5, 2003.
Oct. 28, 2002 International Search Report for Application No. PCT/US2004/040651 filed Dec. 3, 2004.
Nov. 15, 2008 Response to May 28, 2008 non/final rejection in U.S. Appl. No. 10/728,728, filed Dec. 5, 2003.
Dec. 12, 2006 Response to Sep. 13, 2006 non/final rejection in U.S. Appl. No. 10/728,728, filed Dec. 5, 2003.
Dec. 15, 2009 Response to the Examination Report for application No. 05 794 899.4.
Dec. 15, 2009 Response to the Examination Report for application No. 05 794 916.6.
May 28, 2008 Non/final rejection in U.S. Appl. No. 10/728,728, filed Dec. 5, 2003.
Mar. 19, 2008 European Search Report Application No. 05794899.4 filed Sep. 8, 2005.
Jun. 7, 2006 International Preliminary Report on Patentability for International Application No. PCT/US2004/040651 filed Dec. 3, 2004.
Apr. 3, 2007 International Search Report for Application No. PCT/US05/31958 (the PCT counterpart of the parent application) filed Sep. 8, 2005.
Mar. 25, 2008 European Search Report Application No. 05794916.6 filed Sep. 9, 2005.
Mar. 22, 2007 International Preliminary Report in Int'l App. No. PCT/US2005/032054 filed on Sep. 9, 2005.
Jun. 3, 2008 European Patent Office Communication in Euro. App. No. 05 794 916.6 filed on Sep. 9, 2005.

(56) References Cited

OTHER PUBLICATIONS

Dec. 18, 2008 Response to Jun. 3, 2008 European Patent Office Communication in Euro. App. No. 05 794 916.6 filed on Sep. 9, 2005.
Nov. 25, 2008 Response to May 28, 2008 Non/final Rejection in U.S. Appl. No. 10/728,728, filed Dec. 5, 2003.
Feb. 5, 2009 Restriction Requirement in U.S. Appl. No. 11/884,017, filed Jul. 2, 2004.
Mar. 2, 2009 Response to Feb. 5, 2009 Restriction Requirement in U.S. Appl. No. 11/884,017, filed Jul. 2, 2004.
Apr. 17, 2009 Non/final Rejection in U.S. Appl. No. 11/884,017, filed Jul. 2, 2004.
Jan. 10, 2007 Non/final Rejection in U.S. Appl. No. 11/415,659, filed May 2, 2006.
Jun. 11, 2007 Response to Jan. 10, 2007 Non/final Rejection in U.S. Appl. No. 11/415,659, filed May 2, 2006.
Aug. 20, 2007 Final Rejection in U.S. Appl. No. 11/415,659, filed May 2, 2006.
Nov. 7, 2007 Response to Aug. 20, 2007 Final Rejection in U.S. Appl. No. 11/415,659, filed May 2, 2006.
Nov. 16, 2007 Advisory Action in U.S. Appl. No. 11/415,659, filed May 2, 2006.
Feb. 20, 2008 Response to Aug. 20, 2007 Final Rejection in U.S. Appl. No. 11/415,659, filed May 2, 2006.
May 20, 2008 Non/final Rejection in U.S. Appl. No. 11/415,659, filed May 2, 2006.
Nov. 19, 2008 Response to May 20, 2008 Non/final Rejection in U.S. Appl. No. 11/415,659, filed May 2, 2006.
Apr. 6, 2009 Final Rejection in U.S. Appl. No. 11/415,659, filed May 2, 2006.
May 11, 2009 Response to Apr. 6, 2009 Final Rejection in U.S. Appl. No. 11/415,659, filed May 2, 2006.
Jun. 8, 2007 Response to Jan. 8, 2007 Non/final Rejection in U.S. Appl. No. 11/415,764, filed May 2, 2006.
Aug. 20, 2007 Non/final Rejection in U.S. Appl. No. 11/415,764, filed May 2, 2006.
Feb. 20, 2008 Response to Aug. 20, 2007 Non/final Rejection in U.S. Appl. No. 11/415,764, filed May 2, 2006.
Jun. 13, 2008 Non/final Rejection in U.S. Appl. No. 11/415,765, filed May 2, 2006.
Dec. 12, 2008 Response to Jun. 13, 2008 Non/final Rejection in U.S. Appl. No. 11/415,764, filed May 2, 2006.
Apr. 10, 2006 International Search Report for Application No. PCT/US05/32054 (the PCT counterpart of the parent application) filed on Sep. 9, 2005.

\* cited by examiner

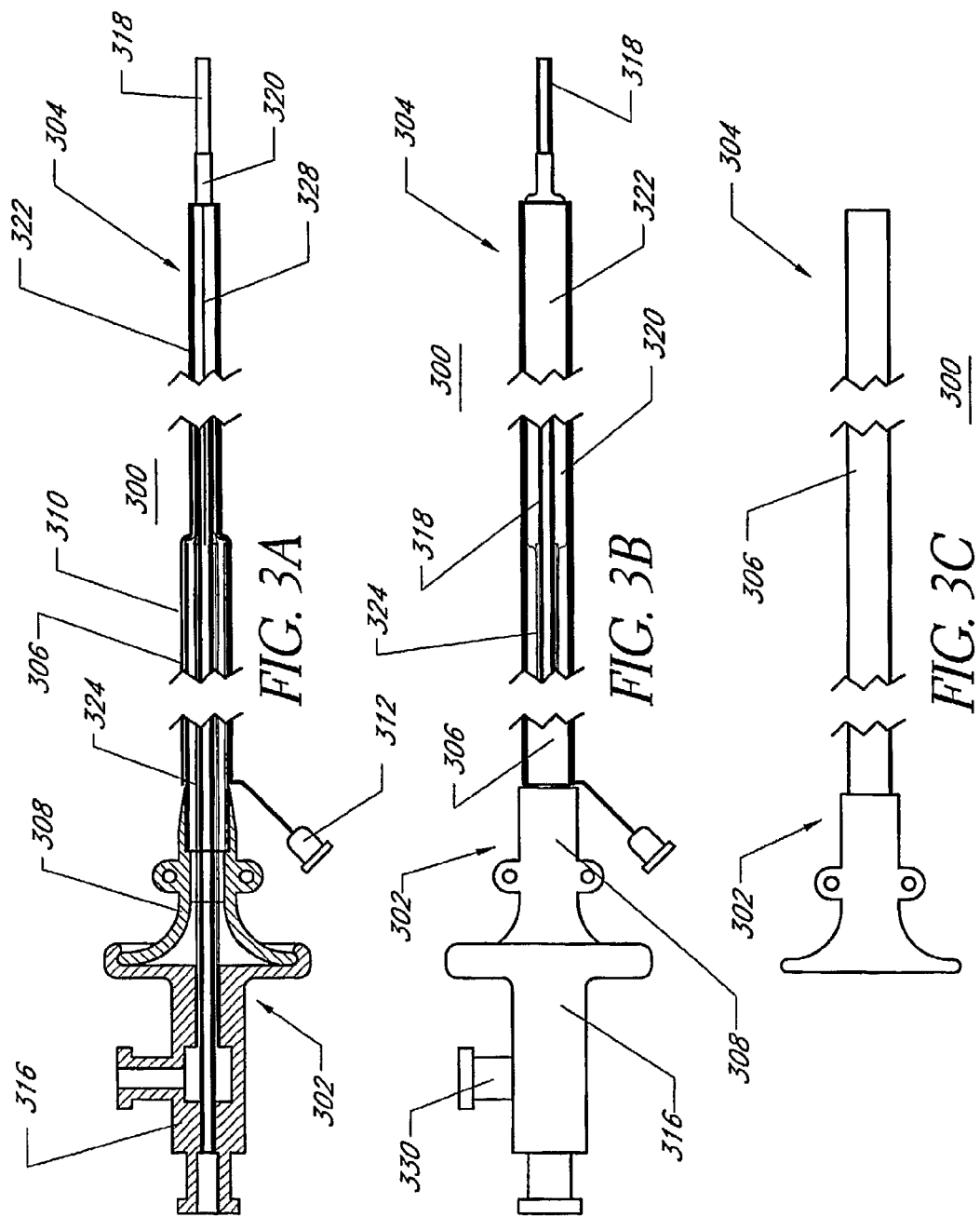

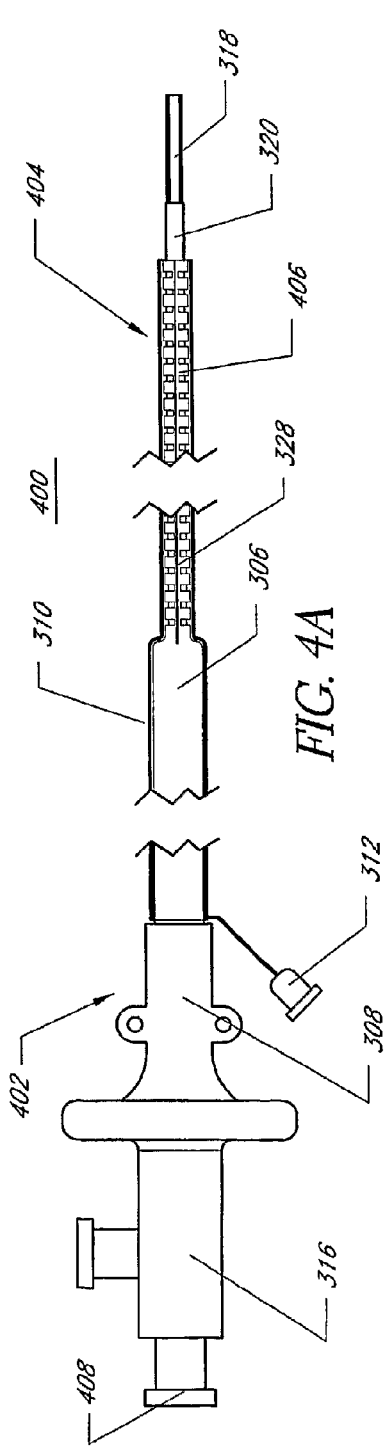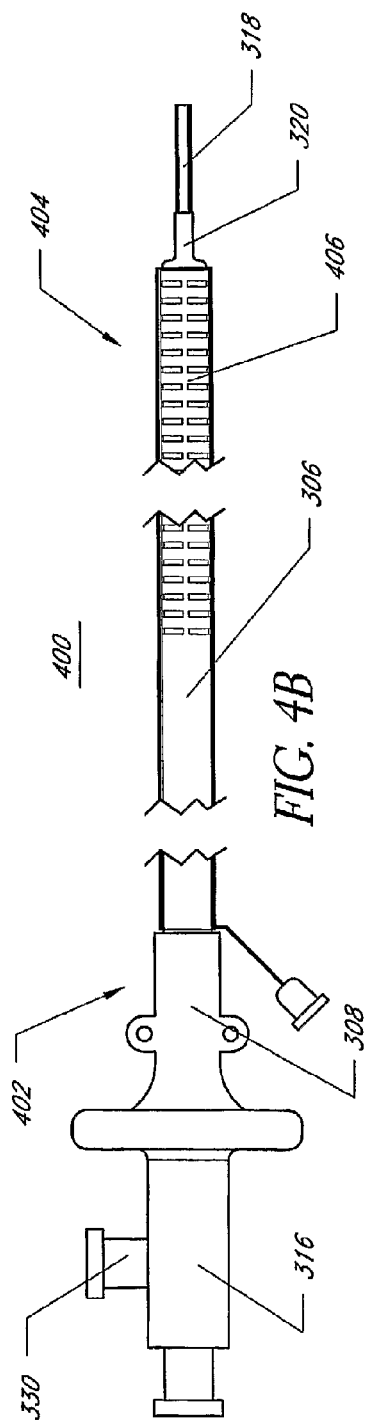

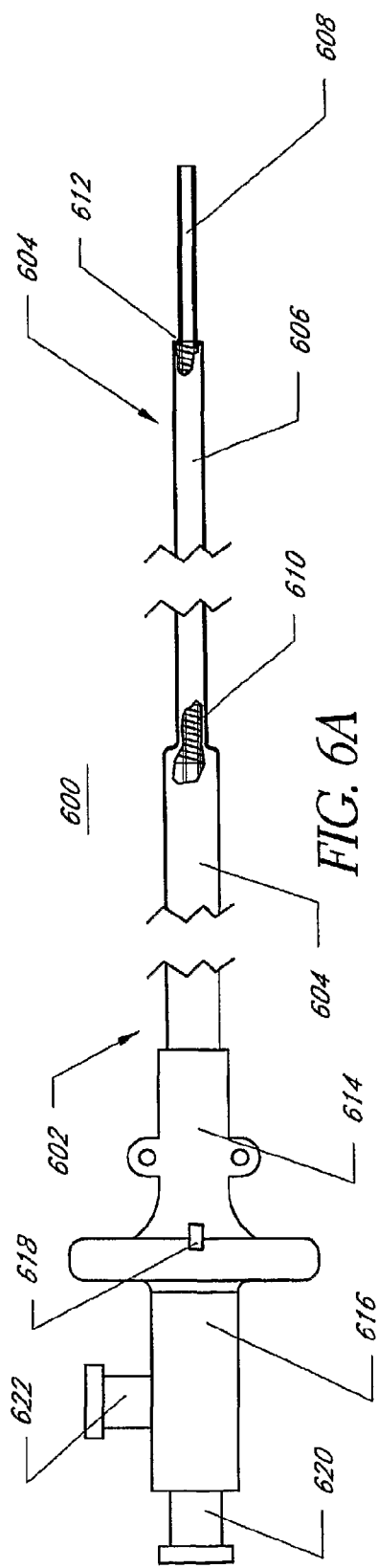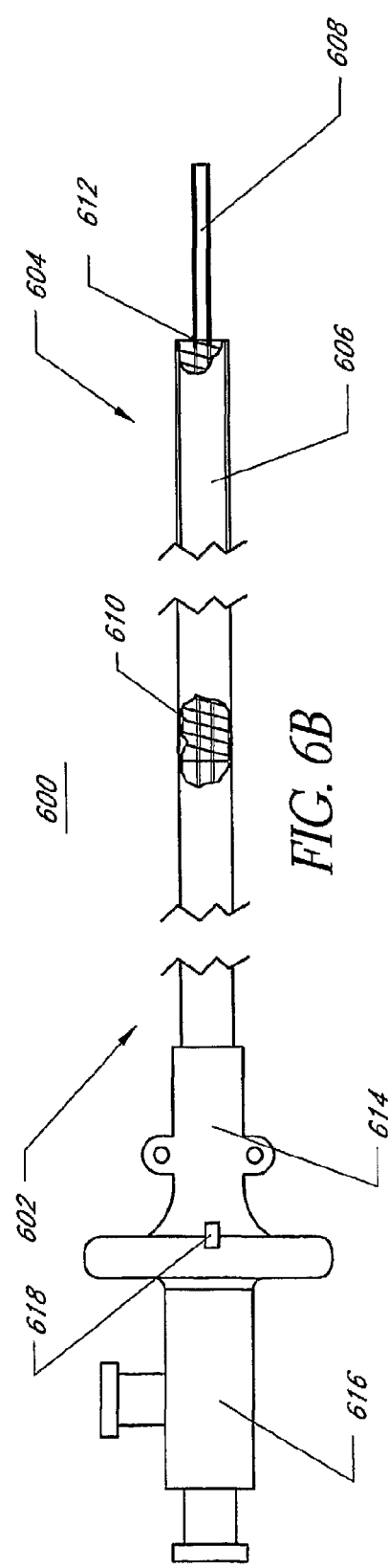

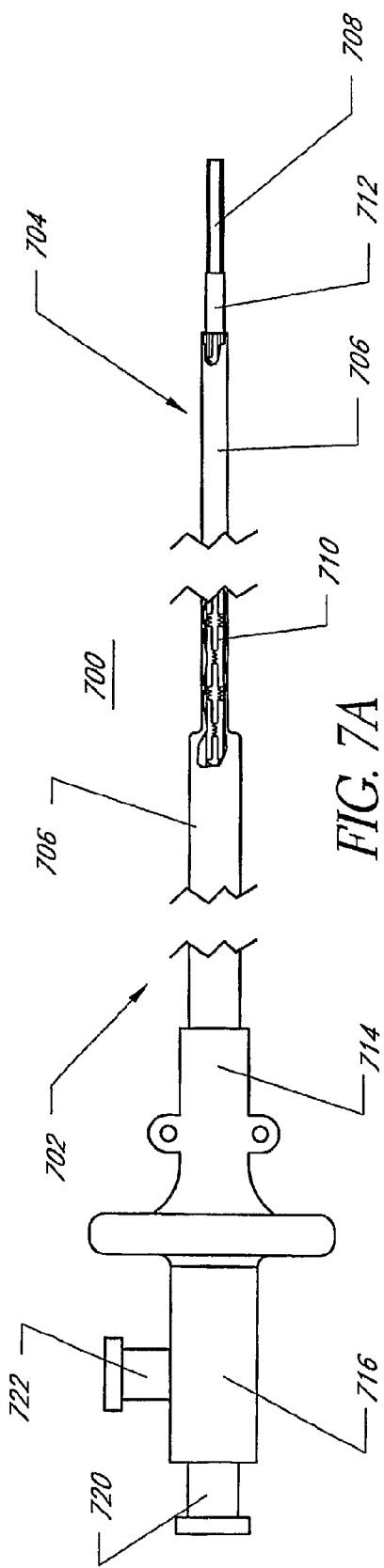
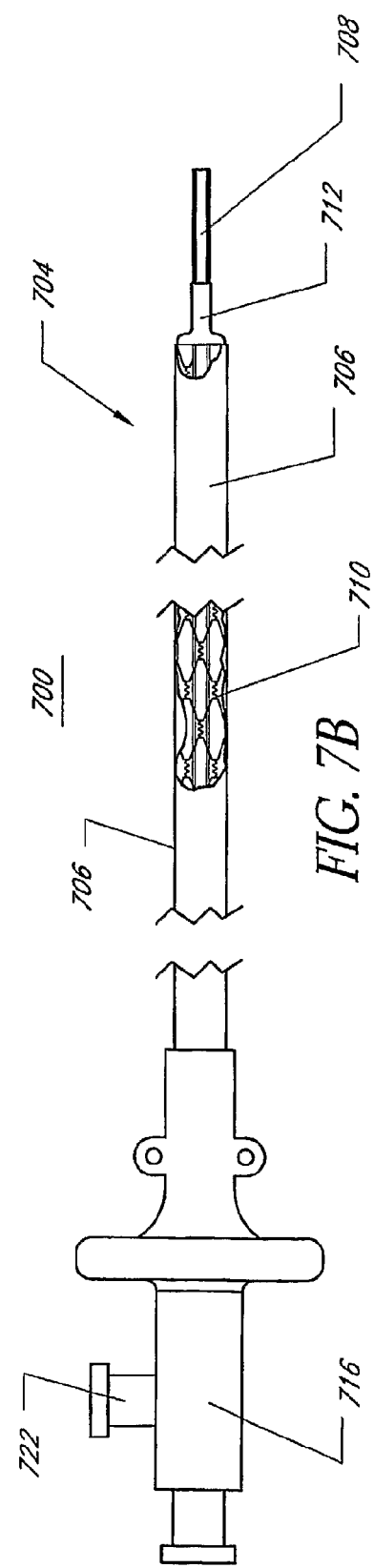

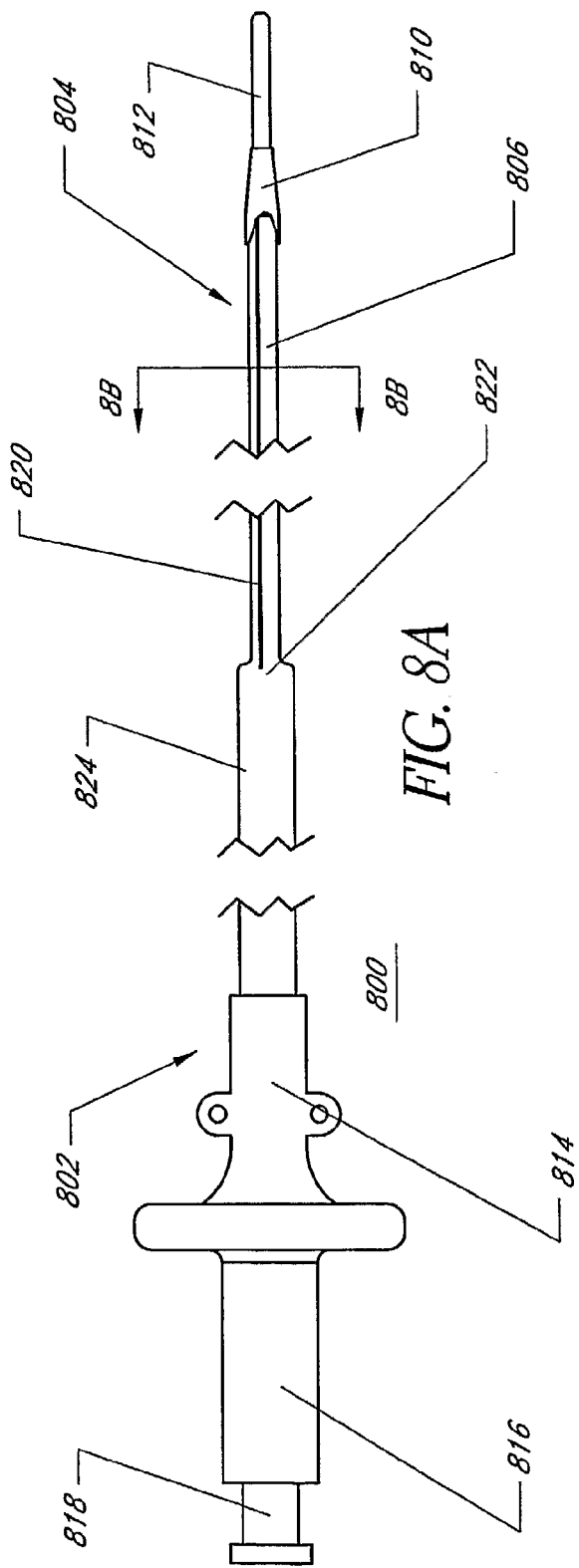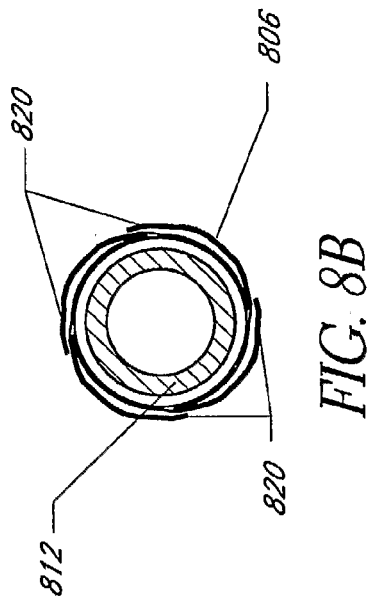
FIG. 8A
FIG. 8B

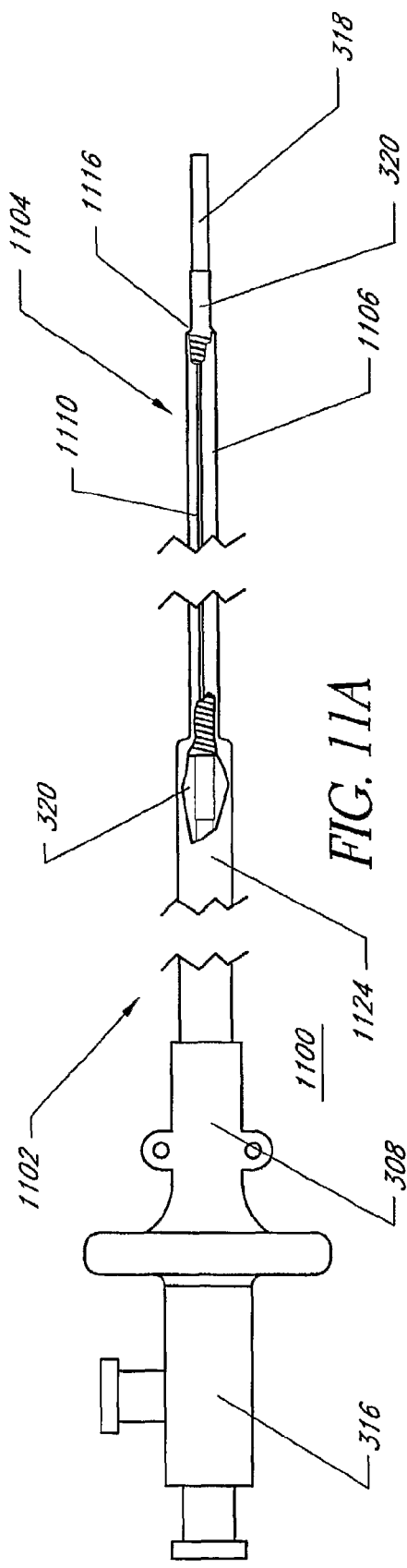
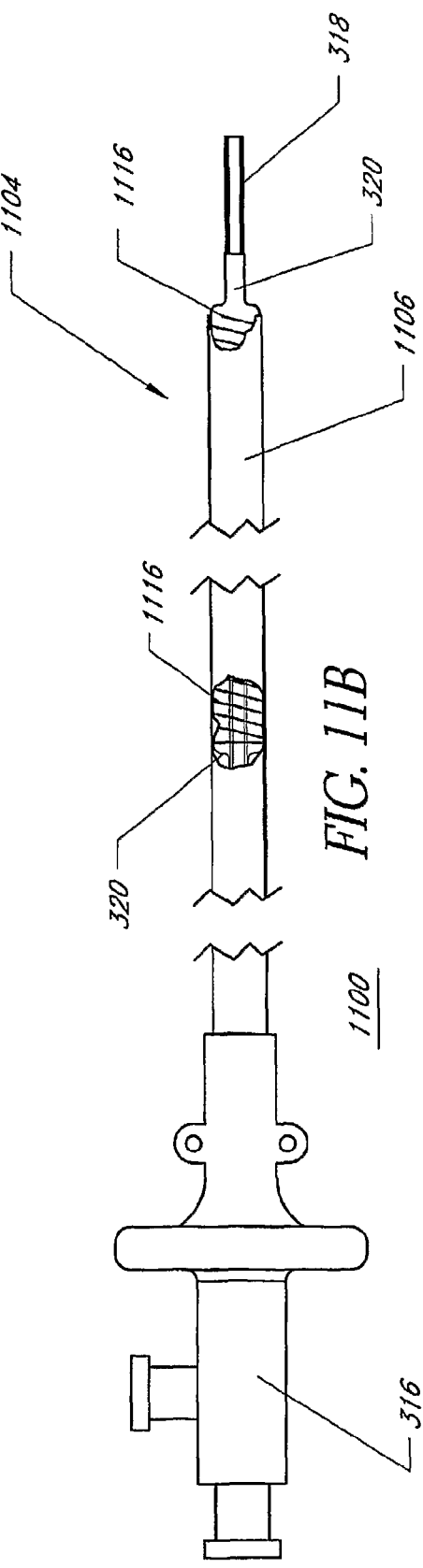

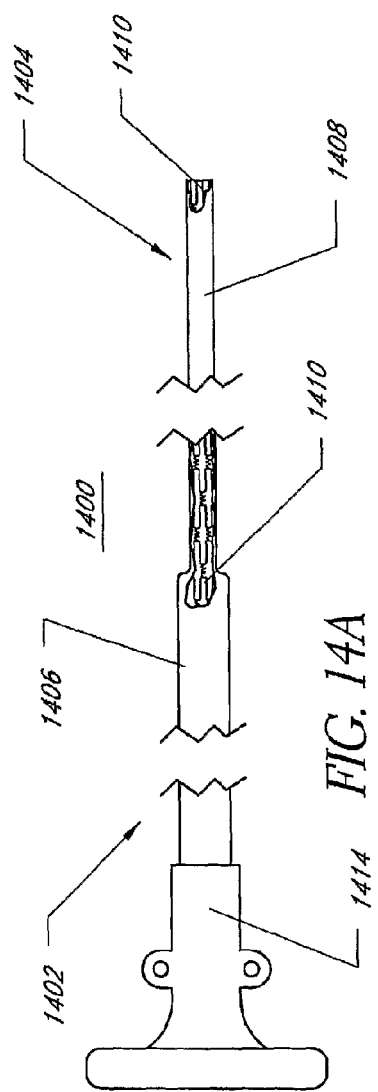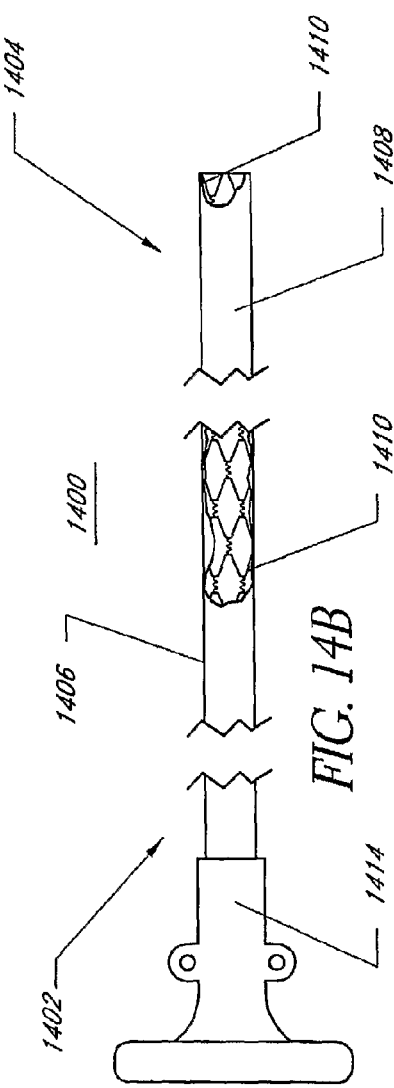

EXPANDABLE TRANSLUMINAL SHEATH

PRIORITY CLAIM

This application is a continuation of U.S. patent application Ser. No. 11/223,897, filed on Sep. 9, 2005, titled "Expandable Transluminal Sheath," which claims priority to U.S. Provisional Application No. 60/608,355, filed on Sep. 9, 2004, titled "Expandable Transluminal Sheath." Each of the foregoing applications is hereby incorporated herein by reference in its entirety.

BACKGROUND OF THE INVENTION

1. Field of the Invention

The present invention relates to medical devices and, more particularly, to methods and devices for accessing the mammalian urinary tract. In one application, the present invention relates to methods and devices for providing access to the ureter and kidney.

2. Description of the Related Art

A wide variety of diagnostic or therapeutic procedures involves the introduction of a device through a natural access pathway. A general objective of access systems, which have been developed for this purpose, is to minimize the cross-sectional area of the access lumen, while maximizing the available space for the diagnostic or therapeutic instrument. These procedures are especially suited for the urinary tract of the human or other mammal. The urinary tract is relatively short and substantially free from the tortuosity found in many endovascular applications.

Ureteroscopy is an example of one type of therapeutic interventional procedure that relies on a natural access pathway. Ureteroscopy is a minimally invasive procedure that can be used to provide access to the upper urinary tract. Ureteroscopy is utilized for procedures such as stone extraction, stricture treatment, or stent placement.

To perform a procedure in the ureter, a cystoscope is placed into the bladder through the urethra. A guidewire is next placed, through the working channel of the cystoscope and under direct visual guidance, into the target ureter. Once guidewire control is established, the cystoscope is removed and the guidewire is left in place. A ureteral sheath or catheter is next advanced through the urethra over the guidewire, through the bladder and on into the ureter. The guidewire may now be removed to permit instrumentation of the ureteral sheath or catheter.

Current techniques involve advancing a flexible, 10 to 18 French, ureteral catheter with integral flexible, tapered obturator over the guidewire. Because axial pressure is required to advance and place each catheter, care must be taken to avoid kinking the tapered catheter during advancement so as not to compromise the working lumen of the catheter through which instrumentation, such as ureteroscopes and stone extractors, must now be placed.

One of the issues that arise during ureteroscopy is the presence of an obstruction or stenosis in the ureter, which is sometimes called a stricture, that prohibits a catheter with a large enough working channel from being able to be advanced into the ureter. Such conditions may preclude the minimally invasive approach and require more invasive surgical procedures in order to complete the task. Urologists may be required to use catheters with sub optimal central lumen size because they are the largest catheters that can be advanced to the proximal end of the ureter. Alternatively, urologists may start with a larger catheter and then need to downsize to a smaller catheter, a technique that results in a waste of time and expenditure. Finally, a urologist may need to dilate the ureter with a dilation system before placing the current devices, again a waste of time and a need for multiple devices to perform the procedure. In most cases, it is necessary for the urologist to perform fluoroscopic evaluation of the ureter to determine the presence or absence of strictures and what size catheter would work for a given patient.

Additional information regarding ureteroscopy can be found in Su, L, and Sosa, R. E., *Ureteroscopy and Retrograde Ureteral Access, Campbell's Urology*, 8th ed, vol. 4, pp. 3306-3319 (2002), Chapter 97. Philadelphia, Saunders, and Moran, M. E., editor, *Advances in Ureteroscopy, Urologic Clinics of North America*, vol. 31, No. 1 (February 2004).

A need therefore remains for improved access technology, which allows a device to be transluminally passed through a relatively small diameter duct, while accommodating the introduction of relatively large diameter instruments. It would be beneficial if a urologist did not need to inventory and use a range of catheter diameters. It would be far more useful if one catheter diameter could fit the majority of patients. Ideally, the catheter would be able to enter a vessel or body lumen with a diameter of 6 to 10 French or smaller, and be able to pass instruments through a central lumen that was 12 to 18 French. These requirements appear to be contradictory but can be resolved by the invention described below.

SUMMARY OF THE INVENTION

Accordingly, one embodiment of the present invention comprises a device adapted for providing therapeutic or diagnostic access to a kidney through the ureter comprising a sheath having a non-expandable proximal end and a radially expandable distal end that can be expanded from an outer diameter of about 10 French or smaller to an outer diameter of greater than about 12 French.

Another embodiment of the present invention comprises an apparatus adapted for instrumenting a body lumen. The device includes a sheath having a proximal end and a distal end and means for radially collapsing the distal end of a sheath and maintaining said radially collapsed configuration. Means are also provided for introducing the sheath into the body lumen while the distal end is in its radially collapsed configuration and for dilating the radially collapsed distal end of the sheath. The sheath also includes means maintaining the dilated configuration of the distal end of the sheath, following dilation by the dilator, means for performing instrumentation, material introduction or withdrawal from the body lumen through the sheath and means for removal of the sheath from the body lumen.

Another embodiment of the present invention comprises a method of instrumenting a body lumen. A dilator is inserted into a sheath that has a radially collapsible distal end. The distal end of the sheath is collapsed radially inward around the dilator such that the distal end of the sheath is smaller in diameter than the proximal end of the sheath. The sheath and dilator are inserted into the body lumen and advanced to a target treatment site. The dilator is expanded and causes the distal end of the sheath to expand to a diameter substantially the same as that of the proximal end of the sheath. The dilator is removed and the central lumen that remains is substantially the same diameter moving from the proximal end to the distal end of the sheath. Instruments or catheters are inserted through the central lumen of the sheath for a therapeutic or diagnostic procedure.

Another embodiment of the present invention comprises an expandable medical access sheath for providing minimally invasive access to body lumens or cavities, length of proximal sheath tubing, said proximal sheath tubing being non-expandable. The sheath includes a length of distal sheath tubing. The distal sheath tubing is collapsed to a diameter smaller than that of the proximal sheath tubing. A transition zone exists between the distal sheath tubing and the proximal sheath tubing. The transition zone tapers between the larger diameter proximal sheath tubing and the smaller diameter distal sheath tubing. A dilator is disposed within both the proximal sheath tubing and the distal sheath tubing. Radial expansion of the dilator causes the distal sheath tubing to expand diametrically to substantially the same inner diameter as that of the proximal sheath tubing.

A transluminal radially expanding access sheath is provided according to an embodiment of the invention. In one embodiment, the radially expanding access sheath is used to provide access to the ureter, kidney, or bladder. In an embodiment, the sheath would have an introduction outside diameter that ranged from 4 to 12 French with a preferred range of 5 to 10 French. The inside diameter of the sheath would be expandable to permit instruments ranging from 10 French to 60 French to pass therethrough, with a preferred range of between 12 and 20 French. The ability to pass the large instruments through a catheter or sheath introduced with a small outside diameter is derived from the ability to expand the distal end of the catheter to create a larger through lumen. The proximal end of the catheter is generally larger to provide for pushability, control, and the ability to pass large diameter instruments therethrough.

Another embodiment of the invention comprises a transluminal access system for providing minimally invasive access to anatomically proximal structures. The system includes an access sheath comprising an axially elongate tubular body that defines a lumen, at least a portion of the distal end of the elongate tubular body being expandable from a first, smaller cross-sectional profile to a second, greater cross-sectional profile. In an embodiment, the first, smaller cross-sectional profile is created by making axially oriented folds in the sheath material. These folds may be in only one circumferential position on the sheath, or there may be a plurality of such folds or longitudinally oriented crimps in the sheath. The folds or crimps may be made permanent or semi-permanent by heat-setting the structure, once folded. In an embodiment, a releasable jacket is carried by the access sheath to restrain at least a portion of the elongate tubular structure in the first, smaller cross-sectional profile. The elongate tubular body is sufficiently pliable to allow the passage of objects having a maximum cross-sectional diameter larger than an inner diameter of the elongate tubular body in the second, greater cross-sectional profile. The adaptability to objects of larger dimension is accomplished by re-shaping of the cross-section to the larger dimension in one direction accompanied by a reduction in dimension in a lateral direction. The adaptability may also be generated through the use of malleable or elastomerically deformable sheath material.

In another embodiment of the invention, a transluminal access system for providing minimally invasive access includes an access sheath comprising an elongate tubular body having a proximal end and a distal end and defining an axial lumen. At least a portion of the distal end of the elongate tubular body is expandable from a first, folded, smaller cross-sectional profile to a second, greater cross-sectional profile. The sheath wall is axially crimped or folded to form the first smaller cross-sectional profile. The sheath wall is cut or transected laterally to form a plurality of axially aligned segments. The transaction may be generated using laser cutting, a blade, or other plastic cutting technology. The plurality of sheath segments is connected using a plurality of thin pliable connector links. Alternatively, the sheath segments may be connected by an outer or inner sheath membrane with elastomeric or axially deformable properties. The sheath segments may also be created by continuously cutting a spiral in the tube thus creating flexibility and linear attachments between sheath elements since the sheath, or a layer of the sheath is continuous from the proximal to the distal end. In this way, the axial flexibility of the access sheath is increased. The outer or inner sheath engages the plurality of sheath segments by mechanical friction or by adherence. In an embodiment, a releasable jacket is carried by the access sheath to restrain at least a portion of the elongate tubular member in the first, smaller cross-sectional profile. The sheath may also be spiral or ribbed cut only partially through the thickness of the wall, for example, only through the outer portion of the wall but not through to the inner lumen of the sheath. This configuration can be used on tubes, especially those of elastomeric nature, to provide kink resistance and bendability while retaining hoop strength.

In another embodiment of the invention, a transluminal access sheath assembly for providing minimally invasive access comprises a sheath that includes an elongate tubular member having a proximal end and a distal end and defining a working inner lumen. At least a portion of the distal end of the elongate tubular member is expandable from a first, smaller cross-sectional profile to a second, greater cross-sectional profile by plastic yield. Thin, plastically deformable materials such as polyethylene are suitable for this application. In another embodiment, the plastically deformable tubular member is replaced by a folded or creased sheath that is expanded by a dilatation balloon or axially translating dilator. An inner member, in an embodiment, generates the force to expand the sheath. The inner member, which can be a dilatation balloon, is removable to permit subsequent instrument passage through the sheath. Longitudinal runners may be disposed within the sheath to serve as tracks for instrumentation and minimize friction while minimizing the risk of catching the instrument on the expandable plastic. Such longitudinal runners are preferably circumferentially affixed within the sheath so as not to shift out of alignment.

Another embodiment of the invention comprises a transluminal access system, for providing minimally invasive access that includes an elongate tubular body that defines a lumen, at least a portion of the distal end of the elongate tubular body being expandable from a first, smaller cross-sectional profile to a second, greater cross-sectional profile. Optionally, a releasable jacket can be carried by the access sheath to restrain at least a portion of the elongate tubular structure in the first, smaller cross-sectional profile. The axially elongate tubular structure is further reinforced by a stent or stent-like support structure. The stent-like support structure is expandable and may be either elastomeric and self-expanding or malleable and require an active dilator for its expansion. The stent-like support structure may also be a coil that is unwound to increase its diameter. The stent-like support structure preferably has very little foreshortening when it is expanded radially. The stent-like support structure is affixed interior to or embedded within at least a part of the wall of the axially elongate tubular structure. An expandable dilating member is positioned within the elongate tubular body and configured to expand the elongate tubular body from the first, smaller cross-sectional profile to the second, greater cross-sectional profile.

Another embodiment of the invention comprises a transluminal access assembly that includes an elongate tubular body that defines an internal lumen. At least a portion of the distal end of the elongate tubular structure is expandable from a first, axially folded smaller cross-sectional profile to a second, greater cross-sectional profile. The elongate tubular structure may be creased or it may be elastomerically or malleably expandable. A releasable jacket is optionally carried by the access sheath to restrain at least a portion of the elongate tubular body in the first, smaller cross-sectional profile. A reinforcing structure fabricated from nickel-titanium alloy such as nitinol, provides the wall support to prevent re-collapse following dilatation. The nitinol can be severely distorted or pinched to form the folds or furls, and still be restored to its initial set-shape. In the first, folded, smaller-cross-sectional profile, the elongate tubular body of one embodiment, includes two creased outer sections that generally face each other.

Another embodiment of the invention comprises a transluminal access sheath system that includes an elongate tubular structure that defines an lumen, at least a portion of the distal end of the elongate tubular structure being expandable from a first, folded, smaller cross-sectional profile to a second, greater cross-sectional profile. The expandable portion of the sheath relies on unfurling longitudinal folds or creases, elastomerically expandable tubes, or a malleably yielding tubular structure surrounding, at least on the outside, a plurality of laterally disposed hoops that can be rotated on edge to form a low profile sheath cross-section or rotated fully laterally to maximize the through lumen of the sheath.

Another embodiment of the invention comprises a transluminal access assembly or access sheath that includes an elongate tubular body that defines an internal lumen. At least a portion of the distal end of the elongate tubular structure is expandable from a first, smaller cross-sectional profile to a second, greater cross-sectional profile. The elongate tubular structure may be creased or folded axially or it may be elastomerically or malleable expandable. A releasable jacket is optionally carried by the access sheath to restrain at least a portion of the elongate tubular body in the first, smaller cross-sectional profile. A reinforcing structure such as a stent, braid, or spiral reinforcement may optionally be incorporated into the wall of the elongate tubular body at the proximal end of the catheter. In this embodiment, the elongate tubular structure comprises, at least along part of its length, a double wall balloon that may be inflated to form a rigid or semi-rigid structure with an internal axial lumen therethrough, a pressurized annular lumen, and an exterior wall that provides at least some level of outward force to be exerted on surrounding tissue. The double wall balloon, located at the distal end of the sheath or catheter, is inflated from the proximal end of the access assembly.

Another embodiment of the invention comprises a transluminal access assembly that includes an elongate tubular body that defines an internal lumen. At least a portion of the distal end of the elongate tubular structure is expandable from a first, smaller cross-sectional profile to a second, greater cross-sectional profile. The elongate tubular structure may be creased or it may be elastomerically or malleable expandable. A releasable jacket is optionally carried by the access sheath to restrain at least a portion of the elongate tubular body in the first, smaller cross-sectional profile. In this embodiment, the elongate tubular structure comprises, at least along part of its length, a braided or counter-wound coil-like structure that may be radially expanded by forced axial compression. The braided or counter-wound coil-like structure can be made to form a rigid or semi-rigid expanded structure with an axial lumen therethrough and an exterior wall that provides at least some level of outward force to be exerted on surrounding tissue. The axial compression, in an embodiment, can be accomplished by pull-wires slidably affixed within, or adjacent to, the wall of the sheath and operated from manipulators located at or near the proximal end of the sheath.

In some embodiments, the proximal end of the access assembly, apparatus, or device is preferably fabricated as a structure that is flexible, resistant to kinking, and further retains both column strength and torqueability. Such structures include tubes fabricated with coils or braided reinforcements and preferably comprise inner walls that prevent the reinforcing structures from being exposed to the inner lumen of the access apparatus. Such proximal end configurations may be single lumen, or multi-lumen designs, with a main lumen suitable for instrument or obturator passage and additional lumens being suitable for control and operational functions such as balloon inflation. Such proximal tube assemblies can be affixed to the proximal end of the distal expandable segments described heretofore. The preferred configuration for the proximal end of the catheter includes an inner layer of thin polymeric material, an outer layer of polymeric material, and a central region comprising a coil, braid, stent or other reinforcement. It is beneficial to create a bond between the outer and inner layers at a plurality of points, most preferably at the interstices or perforations in the reinforcement structure, which is generally fenestrated. The polymeric materials used for the outer wall of the jacket are preferably elastomeric to maximize flexibility of the catheter. The polymeric materials used in the composite catheter inner wall may be the same materials as those used for the outer wall, or they may be different. In another embodiment, a composite tubular structure can be co-extruded by extruding a polymeric compound with a braid or coil structure embedded therein.

In an embodiment of the invention, it is beneficial that the catheter comprise a radiopaque marker or markers. The radiopaque markers may be affixed to the non-expandable portion or they may be affixed to the expandable portion. Markers affixed to the radially expandable portion preferably do not restrain the sheath or catheter from radial expansion or collapse. Markers affixed to the non-expandable portion, such as the catheter shaft of a balloon dilator may be simple rings that are not radially expandable. Radiopaque markers include shapes fabricated from malleable material such as gold, platinum, tantalum, platinum iridium, and the like. Radiopacity can also be increased by vapor deposition coating or plating metal parts of the catheter with metals or alloys of gold, platinum, tantalum, platinum-iridium, and the like. Expandable rings may be fabricated as undulated or wavy rings, or other structures such as are found commonly on stents used for implantation in the body. Expandable structures may also include dots or other incomplete surround shapes affixed to the surface of a sleeve or other expandable shape. Non-expandable structures include circular rings or other structures that completely surround the catheter circumferentially and are strong enough to resist expansion. In another embodiment, the polymeric materials of the catheter or sheath may be loaded with radiopaque filler materials such as, but not limited to, barium sulfate or bismuth salts, at percentages from 5% to 50% by weight, in order to increase radiopacity.

In one embodiment of the invention, in order to enable radial or circumferential expansive translation of the reinforcement, it can be beneficial not to completely bond the inner and outer layers together, thus allowing for some motion of the reinforcement in translation as well as the normal circumferential expansion. Regions of non-bonding may be created by selective bonding between the two layers or by creating non-bonding regions using a slip layer fabricated from polymers such as PTFE, ceramics or metals. Radial expansion capabilities are important because the proximal end needs to transition to the distal expansive end and, to minimize manufacturing costs, the same catheter may be employed at both the proximal and distal end, with the expansive distal end undergoing secondary operations to permit radial or diametric expansion.

In another embodiment, the distal end of the catheter is fabricated using an inner tubular layer, which is thin and lubricious. This inner layer is fabricated from materials such as FEP, PTFE, polyimide, polyamide, polyethylene, polypropylene, and the like. The reinforcement layer comprises a coil, stent, or plurality of expandable or collapsible rings, which are generally malleable and maintain their shape once deformed. The outer layer comprises a tube that is split longitudinally, like a collet, and is capable of collapsing inward radially until the gaps between the tubing are reduced to zero or a small size. This structure is fused or bonded to create a composite unitary structure. The structure is crimped radially inward to a reduced cross-sectional area. A balloon or translation dilator is capable of forced expansion of the reinforcement layer, which provides sufficient strength necessary to overcome any forces imparted by the polymeric tubing. The translation dilator may have a smooth distal end, a tapered distal end, a soft pliable distal end, a distal end that is slit longitudinally to permit inward tapering of the elements, or a combination of any of the aforementioned. The distal end of the translation dilator preferably does not catch or hang up on the interior of the expandable tube because of the modified distal tip configuration.

Another embodiment of the invention comprises an axially elongate sheath with a proximal end, a distal end, and a defined internal lumen. At least a portion of the distal end of the sheath is expandable from a first radially collapsed configuration to a second, radially expanded configuration. The expandable portion of the sheath is comprised of a braid, a plurality of longitudinal runners, a tube with staggered "brickwork" slits running longitudinally, or other radially expandable pattern. The sheath may further comprise an elastomeric outer sleeve about its expandable region fabricated from materials such as, but not limited to, polyurethane, silicone elastomer, C-Flex, latex rubber, or the like. An internal translation dilator is operated from the proximal end of the sheath and is advanced proximally to expand the distal end of the sheath. The outer diameter of the translation dilator is slightly smaller than the inside diameter of the proximal end of the sheath. The translation dilator is slightly rounded or tapered or slit to minimize strain and catching on the interior surfaces of the sheath. Once the translation dilator is advanced into the expandable portion of the sheath, the expandable portion of the sheath expands. The inner lumen of the translation dilator becomes the inner lumen of the sheath along its entire length. If a braided material is used to create the expandable portion of the sheath, it may be beneficial to affix stabilization wires between the distal end of the braid and some portion of the non-expandable portion of the sheath. These stabilization wires may prevent constriction of the braid when the translation dilator is being advanced therethrough.

Another embodiment of the invention comprises a method of providing transluminal access. The method comprises inserting a cystoscope into a patient transurethrally into the bladder. Under direct optical visualization, fluoroscopy, MRI, or the like, a guidewire is passed through the instrument channel of the cystoscope and into the bladder. The guidewire is manipulated, under the visual control described above, into the ureter through its exit into the bladder. The guidewire is next advanced to the appropriate location within the ureter. The cystoscope is next removed, leaving the guidewire in place. The ureteral access sheath is next advanced over the guidewire transurethrally so that its distal tip is now resident in the ureter. The position of the guidewire is maintained carefully so that it does not come out of the ureter and fall into the bladder. A removable obturator with a guidewire lumen can be used to assist with placement of the access sheath into the urinary lumens. The obturator is removed from the access sheath following correct placement. Expansion of the distal end of the access sheath from a first smaller diameter cross-section to a second larger diameter cross-section is next performed, optionally with an expandable member, to permit passage of instruments that would not normally have been able to be inserted into the ureter due to the presence of strictures, stones, or other stenoses. The method further optionally involves releasing the elongate tubular body from a constraining tubular jacket, removing the expandable member from the elongate tubular body; inserting appropriate instrumentation, and performing the therapeutic or diagnostic procedure. Finally, the procedure involves optionally collapsing the elongate tubular body to a cross-sectional profile smaller than the second, greater cross-sectional profile, and removing the elongate tubular body from the patient. Such final reduction in cross-sectional size prior to removal from the patient is optional but may be important in certain patients.

In one embodiment, where the transluminal access sheath is used to provide access to the upper urinary tract, the access sheath may be used to provide access by tools adapted to perform biopsy, urinary diversion, stone extraction, antegrade endopyelotomy, and resection of transitional cell carcinoma and other diagnostic or therapeutic procedures of the upper urinary tract or bladder. Other applications of the transluminal access sheath include a variety of diagnostic or therapeutic clinical situations, which require access to the inside of the body, through either an artificially created, percutaneous access, or through another natural body lumen.

For purposes of summarizing the invention, certain aspects, advantages and novel features of the invention are described herein. It is to be understood that not necessarily all such advantages may be achieved in accordance with any particular embodiment of the invention. The means described herein for accomplishing the procedure can comprise some or all of the elements presented. Thus, for example, those skilled in the art will recognize that the invention may be embodied or carried out in a manner that achieves one advantage or group of advantages as taught herein without necessarily achieving other advantages as may be taught or suggested herein. These and other objects and advantages of the present invention will be more apparent from the following description taken in conjunction with the accompanying drawings.

BRIEF DESCRIPTION OF THE DRAWINGS

A general architecture that implements the various features of the invention will now be described with reference to the drawings. The drawings and the associated descriptions are provided to illustrate embodiments of the invention and not to limit the scope of the invention. Throughout the drawings, reference numbers are re-used to indicate correspondence between referenced elements.

FIG. 3A is a cross-sectional illustration of a radially expandable transluminal catheter or sheath comprising a tube that is folded, at its distal end in longitudinal creases, and a balloon dilator, both of which are in their radially collapsed configuration, according to an embodiment of the invention;

FIG. 3B is a cross-sectional illustration of the radially expandable transluminal sheath of FIG. 3A, wherein the sheath and the dilator are in their radially expanded configuration, according to an embodiment of the invention.

FIG. 3C illustrates a cross-section of the radially expanded transluminal sheath of FIG. 3B, wherein the dilator has been removed, according to an embodiment of the invention;

FIG. 4A is an illustration of a radially expandable transluminal sheath comprising a longitudinally folded sheath and a balloon dilator, wherein the distal portion of the sheath further comprises segmentation to increase flexibility, according to an embodiment of the invention;

FIG. 4B illustrates the radially expandable transluminal sheath of FIG. 4A wherein the segmented distal portion has been expanded by the dilator, according to an embodiment of the invention;

FIG. 6A illustrates a radially expandable transluminal sheath comprising a coil reinforcement that is disposed within an outer sleeve layer, wherein the coil is unwound to cause the sheath to expand, according to an embodiment of the invention;

FIG. 6B illustrates the radially expandable transluminal sheath of FIG. 6A wherein the coil has been unwound to a larger diameter, according to an embodiment of the invention;

FIG. 7A illustrates a radially expandable transluminal sheath comprising a malleable expandable stent-like reinforcement, a balloon dilator, and an expandable sleeve, according to an embodiment of the invention;

FIG. 7B illustrates the radially expandable transluminal sheath of FIG. 7A wherein the distal section has been expanded by the balloon dilator, according to an embodiment of the invention;

FIG. 8A illustrates a side view of a radially expandable transluminal sheath in its small diameter configuration, comprising an unfurling unsupported sleeve through which instruments may be passed, according to an embodiment of the invention;

FIG. 8B illustrates a lateral cross-section of the distal end of the sheath illustrated in 8A, showing the sheath furled about the obturator, according to an embodiment of the invention;

FIG. 11A illustrates a radially expandable transluminal sheath comprising a reinforcing coil or other winding embedded within a sleeve that further comprises one or more longitudinal folds, and a balloon dilator, according to an embodiment of the invention. The distal end of the sheath, comprising this structure, is crimped or compressed radially inward for delivery to the patient;

FIG. 11B illustrates the expandable sheath of FIG. 11A wherein a balloon dilator has been used to expand the distal end of the sheath radially outward;

FIG. 14A illustrates a radially expandable transluminal sheath comprising a self-expanding metallic reinforcing structure and an unfurling or elastomeric sleeve, according to an embodiment of the invention;

FIG. 14B illustrates the expandable sheath of FIG. 14A wherein the self expanding stent has expanded the distal portion of the sheath, according to an embodiment of the invention;

DETAILED DESCRIPTION OF THE PREFERRED EMBODIMENTS

The invention may be embodied in other specific forms without departing from its spirit or essential characteristics. The described embodiments are to be considered in all respects only as illustrative and not restrictive. The scope of the invention is therefore indicated by the appended claims rather than the foregoing description. All changes that come within the meaning and range of equivalency of the claims are to be embraced within their scope.

As set forth herein, in the description of the invention the terms catheter or a sheath will be used and can be described as being an axially elongate hollow tubular structure having a proximal end and a distal end. The tubular structure does not necessarily have a circular cross-section. The axially elongate structure further has a longitudinal axis and has an internal through lumen that extends from the proximal end to the distal end for the passage of instruments, fluids, tissue, or other materials. As is commonly used in the art of medical devices, the proximal end of the device is that end that is closest to the user, typically a surgeon or interventionalist. The distal end of the device is that end is closest to the patient or is first inserted into the patient. A direction being described as being proximal to a certain landmark will be closer to the surgeon, along the longitudinal axis, and further from the patient than the specified landmark. The diameter of a catheter is often measured in "French Size" which is 3 times the diameter in millimeters (mm). For example, a 15 French catheter is 5 mm in diameter. The French size is designed to correspond to the circumference of the catheter in mm and is often useful for catheters that have non-circular cross-sectional configurations.

Figure 1:
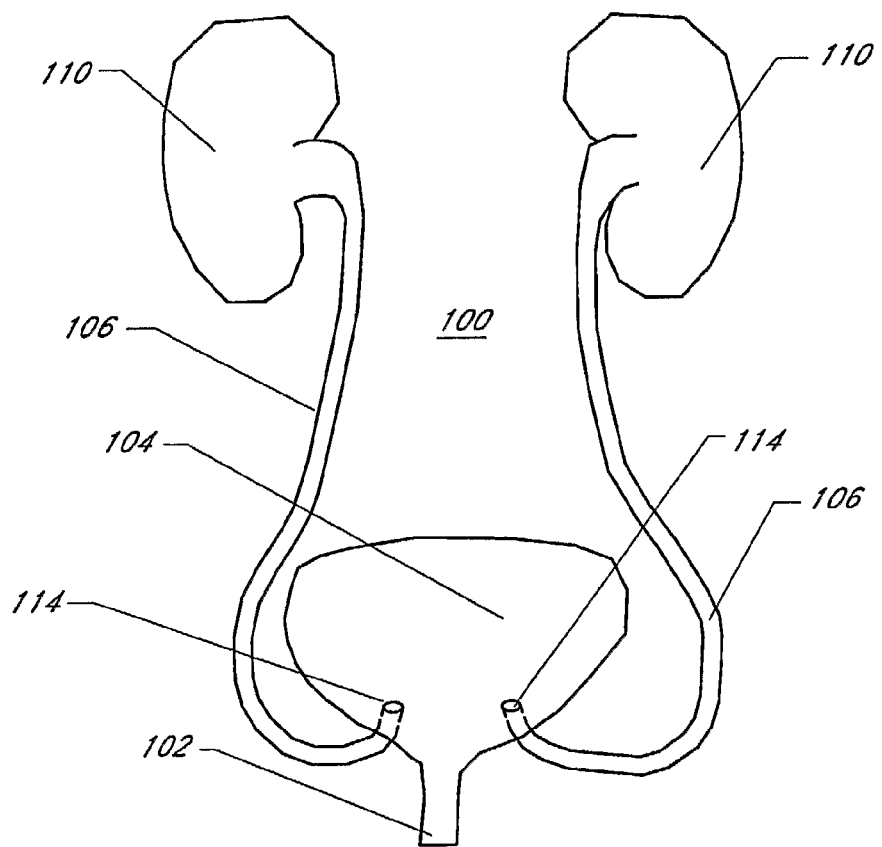
FIG. 1 is a front view schematic representation of the urethra, bladder and ureter.

FIG. 1 is a schematic frontal illustration of a urinary system 100 of the human comprising a urethra 102, a bladder 104, a plurality of ureters 106, a plurality of kidneys 110 and a plurality of entrances 114 to the ureter from the bladder. In this illustration, the left anatomical side of the body is toward the right of the illustration.

Referring to FIG. 1, the urethra 102 is lined on its interior by urothelium. Generally, the internal surfaces of the urethra 102, the bladder 104, and ureters 106 are considered mucosal tissue. The urethra 102 is relatively short in women and may be long in men since it runs through the entire length of the penis. The circumference of the unstretched urethra 102 is generally in the range of pi times 8 mm, or 24 mm, although the urethra 102 generally approximates the cross-sectional shape of a slit when no fluid or instrumentation is resident therein. The bladder 104 has the capability of holding between 100 and 300 cc of urine or more. The volume of the bladder 104 increases and decreases with the amount of urine that fills therein. During a urological procedure, saline is often infused into the urethra 102 and bladder 104 thus filling the bladder 104. The general shape of the bladder 104 is that of a funnel with a dome shaped top. Nervous sensors detect muscle stretching around the bladder 104 and a person generally empties their bladder 104, when it feels full, by voluntarily relaxing the sphincter muscles that surround the urethra 102. The ureters 106 operably connect the kidneys 110 to the bladder 104 and permit drainage of urine that is removed from the blood by the kidneys 110 into the bladder 104. The diameter of the ureters 106 in their unstretched configuration approximates a round tube with a 4 mm diameter, although their unstressed configuration may range from round to slit-shaped. The ureters 106 and the urethra 102 are capable of some expansion with the application of internal forces such as a dilator, etc. The entrance 114 to each of the normally two ureters 106 is located on the wall of the bladder 104 in the lower region of the bladder 104.

Figure 2:
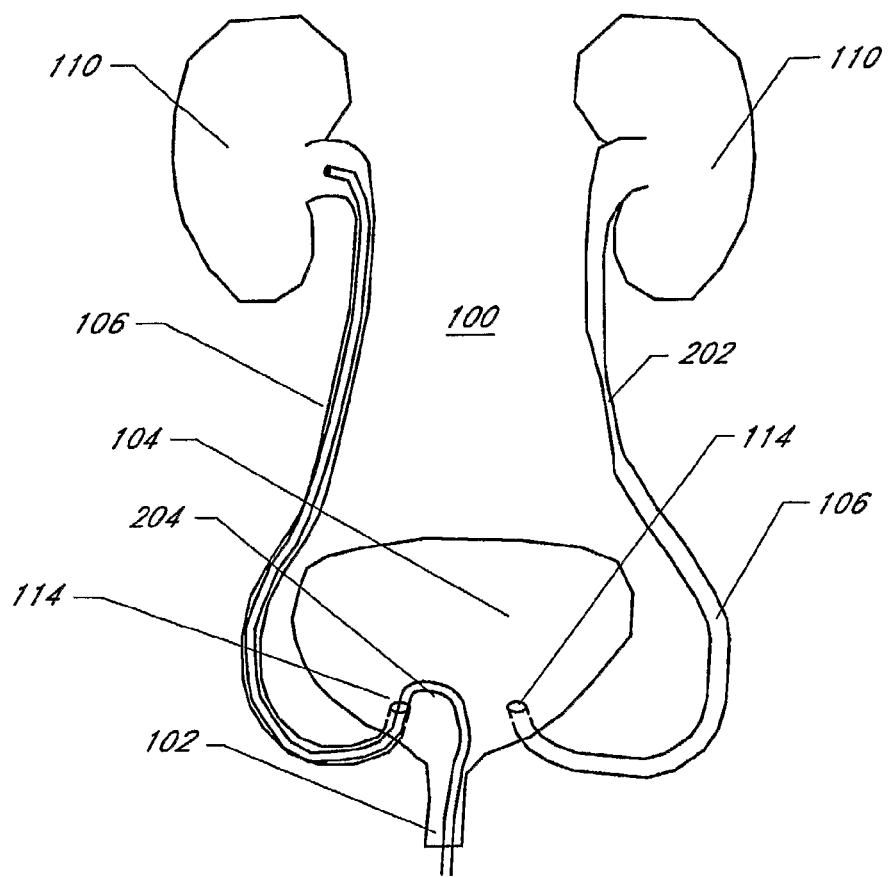
FIG. 2 is a front view schematic representation of the urethra, bladder and ureter with a catheter passed into the ureter by way of the urethra.

FIG. 2 is a schematic frontal illustration, looking in the posterior direction from the anterior direction, of the urinary system 100 comprising the urethra 102, the bladder 104, a plurality of ureters 106 having entrances 114, a plurality of kidneys 110, a stricture 202 in the left ureter, and further comprising a catheter 204 extending from the urethra 102 into the right kidney 110. In this illustration, the left anatomical side of the body is toward the right of the illustration.

Referring to FIG. 2, the stricture 202 may be the result of a pathological condition such as an infection. The stricture may also be the result of iatrogenic injury such as that attributed to a surgical instrument or catheter that caused damage to the wall of the ureter 106. The stricture 202 may be surrounded by fibrous tissue and may prevent the passage of instrumentation that would normally have passed through a ureter 106. The catheter 204 is exemplary of the type used to access the ureter 106 and the kidney 110, having been passed transurethrally into the bladder 104 and on into the ureter 106. A catheter routed from the urethra 102 into one of the ureters 106 may turn a sharp radius within the open unsupported volume of the bladder 104. The radius of curvature necessary for a catheter to turn from the urethra 102 into the ureter 106 may be between 1 cm and 10 cm and in most cases between 1.5 cm and 5 cm. The catheter is generally first routed into the ureter 106 along a guidewire that is placed using a rigid cystoscope. The rigid cystoscope, once it is introduced, straightens out the urethra 102 and is aimed close to the entrance 114 to the ureter 106 to facilitate guidewire placement through the working lumen of the cystoscope.

FIG. 3A illustrates a longitudinal view of an expandable transluminal sheath 300 adapted for use in the urinary system 100 of FIGS. 1 and 2. The front section of the sheath 300 is depicted in exterior view and not in cross-section. The proximal region 302 and the central region are shown in longitudinal cross-section. The transluminal catheter 300 comprises a proximal end 302 and a distal end 304. The proximal end 302 further comprises a proximal sheath tube 306, a sheath hub 308, a sleeve 310, a sleeve grip 312, an inner catheter shaft 318, an outer catheter shaft 324, and a catheter hub 316. The distal end 304 further comprises a distal sheath tube 322, which is folded longitudinally into one or more flutes or creases 328, the inner catheter shaft 318, and a balloon 320.

Referring to FIG. 3A, the proximal end 302 generally comprises the proximal sheath tube 306 that is permanently affixed to the sheath hub 308. The sleeve 310 is tightly wrapped around the proximal sheath tube 306 and is generally able to be split lengthwise and be removed or disabled as a restraint by pulling on the sleeve grip 312 that is affixed to the sleeve 310. The sleeve 310 is generally fabricated from transparent material and is shown so in FIGS. 3A and 3B. The proximal end further comprises the inner catheter shaft 318, the outer catheter shaft 324, and the catheter hub 316. The catheter hub 316 allows for gripping the dilator and it allows for expansion of the dilatation balloon 320 by pressurizing an annulus between the inner catheter shaft 318 and the outer catheter shaft 324, said annulus having openings into the interior of the balloon 320. The balloon 320 is bonded, at its distal end, either adhesively or by fusion, using heat or ultrasonic energy, to the inner catheter shaft 318. The proximal end of the balloon 320 is bonded or welded to the outer catheter shaft 324. Alternatively, pressurization of the balloon 320 can be accomplished by pressurizing a lumen in the inner or outer catheter shafts 318 or 324, respectively, said lumen being operably connected to the interior of the balloon 320 by openings or scythes in the catheter tubing. The distal end 304 generally comprises the distal sheath tube 322 which is folded into flutes or creases 328 running along the longitudinal axis and which permit the area so folded to be smaller in diameter than the sheath tube 306. The inner catheter shaft 318 comprises a guidewire lumen that may be accessed from the catheter hub 316 and passes completely through to the distal tip of the catheter shaft 318. The guidewire lumen is preferably able to contain guidewires up to and including 0.038-inch diameter devices.

The distal end 304 further comprises the catheter shaft 318 and the dilatation balloon 320. The catheter hub 316 may removably lock onto the sheath hub 308 to provide increased integrity to the system and maintain longitudinal relative position between the catheter shaft 318 and the sheath tubing 322 and 306. The catheter shaft 318 and the balloon 320 are slidably received within the proximal sheath tube 306. The catheter shaft 318 and balloon 320 are slidably received within the distal sheath tube 322 when the distal sheath tube 322 is radially expanded but are frictionally locked within the distal sheath tube 322 when the tube 322 is radially collapsed. The outside diameter of the distal sheath tube 322 ranges from 4 French to 16 French in the radially collapsed configuration with a preferred size range of 5 French to 10 French. The outside diameter is critical for introduction of the device. Once expanded, the distal sheath tube 322 has an inside diameter ranging from 8 French to 20 French. The inside diameter is more critical than the outside diameter once the device has been expanded. The wall thickness of the sheath tubes 306 and 322 ranges from 0.002 to 0.030 inches with a preferred thickness range of 0.005 to 0.020 inches.

FIG. 3B illustrates a cross-sectional view of the sheath 300 of FIG. 3A wherein the balloon 320 has been inflated causing the sheath tube 322 at the distal end 304 to expand and unfold the flutes 328. The distal sheath tube 322 has the properties of being able to bend or yield, especially at crease lines, and maintain its configuration once the forces causing the bending or yielding are removed. The proximal sheath tube 306 is affixed to the sheath hub 308 by insert molding, bonding with adhesives, welding, or the like. The balloon 320 has been inflated by pressurizing the annulus between the inner tubing 318 and the outer tubing 324 by application of an inflation device at the inflation port 330 on the catheter hub 316. The pressurization annulus empties into the balloon 320 at the distal end of the outer tubing 324. Exemplary materials for use in fabrication of the distal sheath tube 322 include, but are not limited to, polytetrafluoroethylene (PTFE), fluorinated ethylene polymer (FEP), polyethylene, polypropylene, polyethylene terephthalate (PET), and the like. A wall thickness of 0.008 to 0.012 inches is generally suitable for a device with a 16 French OD while a wall thickness of 0.019 inches is appropriate for a device in the range of 36 French OD. The resulting through lumen of the sheath 300 is generally constant in French size going from the proximal end 302 to the distal end 304. The balloon 320 is fabricated by techniques such as stretch blow molding from materials such as PET, nylon, irradiated polyethylene, and the like.

FIG. 3C illustrates a cross-sectional view of the sheath 300 of FIG. 3B wherein the catheter shaft 318, the balloon 320, and the catheter hub 316 have been withdrawn and removed leaving the proximal end 302 and the distal end 304 with a large central lumen capable of holding instrumentation. The sleeve 310 and the sleeve grip 312 have also been removed from the sheath 300. The shape of the distal sheath tube 322 may not be entirely circular in cross-section, following expansion, but it is capable of carrying instrumentation the same size as the round proximal tube 306. Because it is somewhat flexible and further is able to deform, the sheath 300 can hold noncircular objects where one dimension is even larger than the round inner diameter of the sheath 300. The balloon 320 is preferably deflated prior to removing the catheter shaft 318, balloon 320 and the catheter hub 316 from the sheath 300.

FIG. 4A illustrates a side view of a transluminal expandable sheath 400 comprising a proximal end 402 and a distal end 404. The sheath 400 further comprises a dilator hub 316, a dilator tube 318, a dilator balloon 320, a sheath tube 306, a sheath hub 308, an external sleeve 310, a sleeve grip 312, a proximal guidewire lumen connector 408, and a plurality of slots, disconnections, or perforations 406. The diametrically compressed sheath tube 306 comprises one or more longitudinal folds 328.

Referring to FIG. 4A, the sheath 400 comprises slots 406 that permit bending and flexing of the sheath tube 306. The slots 406 may exist on the proximal part of the sheath tube 306, the distal part of the sheath tube 306, or both. The slots 406 may totally separate the sheath tube 306 adjacent segments or bendable members may interconnect the sheath tube segments. The bendable members may be disposed in one circumferential location, as a backbone, or they may be distributed around the circumference of the sheath, one or two per slot so as to allow bending in a given plane. Bendable members connecting two segments may be located at a different circumferential location relative to those connecting other segments to allow for bending in more than one plane. The segments and their separating slots 406 are configured so that the segments still retain the one or more longitudinal folds or wings 328 which permit the diametric expansion of the sheath 400 upon inflation of the balloon 320. In the illustrated embodiment, the longitudinal fold 328 is shown aligned on the backbone connecting adjacent slots 406. In another embodiment, the segments, which are present to increase flexibility and bendability of the sheath 400, are replaced by a spiral pattern that is cut completely through the wall of the sheath. The spiral pattern can run continuously from the proximal end of the sheath to the distal end of the sheath 400 or from an intermediate location to the distal end of the sheath 400. In yet another embodiment, the spiral pattern may be incompletely, or only partially, cut through the outer wall of the sheath tube 306. This configuration increases the flexibility of the sheath tube 306 and the thicker areas serve to minimize kinking. The sheath tube 306 is fabricated preferably from materials with some elasticity. Candidate materials include, but are not limited to, Hytrel, silicone elastomer, polyurethane, and the like.

FIG. 4B illustrates the sheath 400 of FIG. 4A wherein the balloon 320 has been inflated and has expanded the sheath tube 306 at the distal end 404 of the sheath 400. The proximal end 402 of the sheath appears unchanged in this illustration. Note that the slots 406 have unfolded with the tube 306 but have not expanded longitudinally. In the illustrated embodiment, the slots 406 incompletely circumscribe the sheath tube 306 leaving a backbone or flexible connection between rings of the sheath tube 306. Expansion of the balloon 320 is accomplished by attaching an inflation device (not shown) to the balloon inflation port 330 on the dilator hub 316. The balloon inflation port 330 is operably connected and sealed to the annulus between an inner dilator tube 318 and an outer dilator tube 324 (not shown) so that fluid input into the balloon inflation port 330 flows distally and empties into the balloon 320, whose proximal seal is affixed to the outside of the outer dilator tube (not shown). Alternatively, inflation pressure is carried by a central lumen on a valved catheter, to seal the guidewire at the distal tip, or by one of a plurality of lumens in a central catheter shaft and is transmitted into the balloon through scythes in the catheter shaft to open the pressure lumen to the balloon interior. This balloon dilator construction is appropriate for most of the embodiments of the invention that rely on a balloon dilator. The slots 406 permit bendability and flexibility of the catheter in the radially expanded configuration as well as the radially contracted configuration of FIG. 4A. In another embodiment, the slots 406 are fabricated to cut completely through the wall of one tube while a concentrically affixed composite tubular structure provides the interconnectivity that keeps the sheath tube 306 from separating under tension. In this embodiment, the slots are cut through a material with little elasticity, such as PET. The composite structure may use an inner, or outer, tube fabricated from Pebax, Hytrel, silicone elastomer, C-Flex, polyurethane, or other elastomeric material.

Figure 5A:
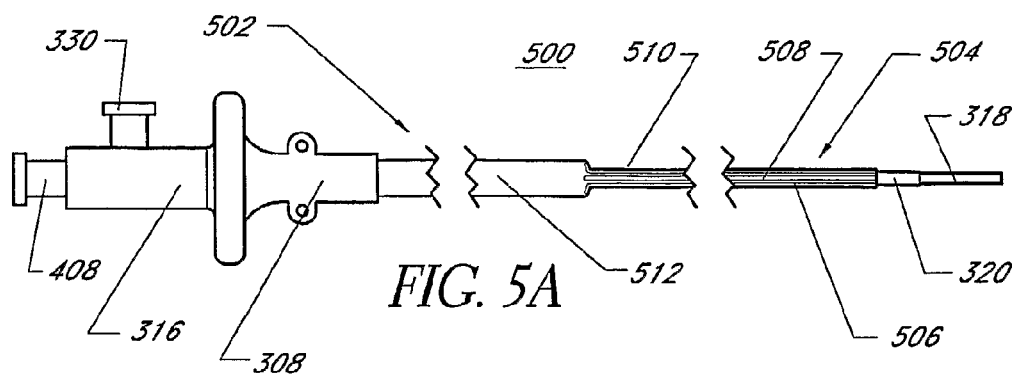
FIG. 5A is an illustration of a radially expandable transluminal sheath further comprising a plurality of longitudinally disposed runners, an irreversibly stretchable outer wall, and a balloon dilator, according to an embodiment of the invention.

FIG. 5A illustrates a side view of a sheath 500 comprising a proximal section 502 and a distal section 504. The distal section 504 comprises a length of dilator tubing 318, a dilator balloon 320, and an outer stretchable layer 510. The distal section 504 further may comprise optional longitudinal runners 506 separated by longitudinal slits or slots 508. The proximal section 502 comprises a proximal sheath cover 512, a sheath hub 308 and a dilator hub 316, further comprising a guidewire port 408 and a balloon inflation connector 330.

Referring to FIG. 5A, the outer stretchable layer 510 is disposed similarly as the wall 306 of the sheath 300 of FIG. 3A. The stretchable layer 510 can be affixed, at its proximal end, to the distal end of the proximal sheath cover 512, which is non-expansible and surrounds the sheath 500 at its proximal end. The internal lumen of the stretchable layer 510 is operably connected to the inner working lumen of the proximal sheath cover 512. The outer stretchable layer 510 may be constructed from materials that are plastically deformable such that the circumference is irreversibly increased by expansion of the dilator balloon 320 and the outward forces created thereby. The wall thickness of the outer stretchable layer 510 will generally decrease as the outer stretchable layer 510 is dilated. The outer stretchable layer 510, once dilated, will generally provide little hoop strength against collapse and serves as the liner of a potential space lumen. The optional longitudinal runners 506, separated by the slits 508, provide a reduced friction track for the passage of instrumentation within the outer stretchable layer 510. The runners 506 can be fabricated from materials such as, but not limited to, PTFE, FEP, PET, stainless steel, cobalt nickel alloys, nitinol, titanium, polyamide, polyimide, polyethylene, polypropylene, and the like. The runners 506 may further provide column strength against collapse or buckling of the outer stretchable layer 510 when materials such as calcific stones or other debris is withdrawn proximally through the sheath 500. The runners 506 may be free and unattached or they may be affixed to the interior of the stretchable layer 510 using adhesives, welding, or the like. The guidewire port 408 is generally configured as a Luer lock connector or other threaded or bayonet mount and the guidewire is inserted therethrough into the guidewire lumen of the dilator tubing 318 to which the guidewire port 408 is operably connected. The guidewire port 408 is preferably integrally fabricated with the dilator hub 316 but may be a separately fabricated item that is affixed to the dilator hub 316. A Tuohy-Borst or other valved fitting is easily attached to such connectors to provide for protection against loss of fluids, even when the guidewire is inserted.

Figure 5B:
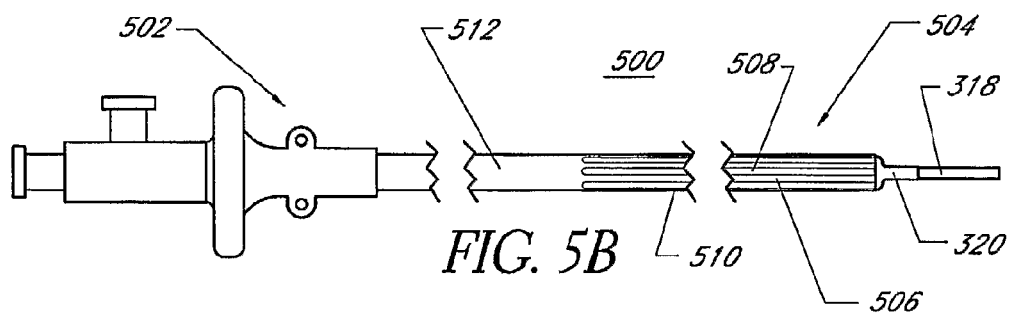
FIG. 5B illustrates the transluminal sheath of FIG. 5A wherein the distal section has been expanded by a balloon dilator, according to an embodiment of the invention.

FIG. 5B illustrates the sheath 500 of FIG. 5A wherein the balloon 320 has dilated the distal section 504 diametrically. The proximal sheath cover 512 is unchanged but the longitudinal runners 506 have become expanded and the longitudinal slits or slots 508 have become wider. The outer stretchable layer 510 of the distal section 504 has stretched permanently to increase the distance circumferentially between the longitudinal slits or slots 508. The resultant distal section 504 is relatively unsupported by the thin wall of the sheath tubing 510 but may be suitable for instrument passage.

Figure 5C:
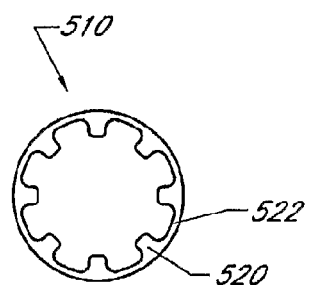
FIG. 5C illustrates a lateral cross-section of the distal portion of the transluminal sheath of FIG. 5A wherein the sheath covering comprises flutes or longitudinally disposed lines of increased thickness, according to an embodiment of the invention.

FIG. 5C illustrates a lateral cross-section of the distal end 504 of another embodiment of the sheath 500. In this embodiment, the outer stretchable layer 510 covering the distal section 504 is fabricated with flutes 520 on the interior, or exterior, surface. Interior flutes 520 are the preferred embodiment in this case. The flutes 520 represent longitudinally running increases in wall thickness of the stretchable layer 510 which are separated by longitudinally running regions of decreased wall thickness 522. The flutes 520 are generally integral to the outer stretchable layer 510. The flutes 520 are generally created by fabricating an extrusion die with slots that permit the polymer to extrude with ridges thereon. The flutes 520 may facilitate folding and minimize damage to optical scopes, such as ureteroscopes, angioscopes, and the like, when inserted therethrough, due to debris scratching the lens when the scope is advanced or retracted. When the stretchable layer 510 is dilated, the region of decreased wall thickness 522 between the flutes 520 will preferentially stretch because of the increased strength of the flutes 520. In this embodiment, more circumferentially uniform stretching of the stretchable layer 510 is possible. It is important to minimize circumferential unevenness of the stretching since balloon dilators will generally impart unevenness in an object being dilated, such as a stent, unless steps are taken to even this process out.

FIG. 6A illustrates a side view of an expandable sheath 600 comprising a proximal end 602 and a distal end 604. The sheath 600 further comprises an outer covering 606, a central torque rod 608, a coil support 610, an engagement catch 612, a sheath hub 614, a torque handle 616, a lock 618, a guidewire port 620, and a fluid infusion port 622. The distal end 604 has a reduced diameter relative to that of the proximal end 602. In this embodiment, the outer covering 606 is either an elastomer or a furled substantially non-distensible material.

Referring to FIG. 6A, the coil support 610 is disposed interior to the outer covering 606 primarily at the distal end 604 of the sheath 600. The engagement catch 612 is affixed to the distal end of the coil support 610 and engages features affixed to the distal end of the central torque rod 608. The torque handle 616 is affixed to the proximal end of the central torque rod 608. The torque handle 616 and the torque rod 608 rotate within the outer covering 606. The torque handle 616 can have friction, ratcheting, or other locking mechanisms 618 to maintain rotational position of the torque handle 616 relative to the sheath hub 614, in which it rotates concentrically. Rotation of the torque handle 616 and attached torque rod 608 relative to the sheath hub 614 is performed manually or with the use of electric, hydraulic, or pneumatic drive systems. The sheath hub 614 is affixed to the proximal end of the outer covering 606. The fluid infusion port 622 is operably connected to the inner lumen of the central torque rod 608, which is hollow, thus allowing fluid to be injected or withdrawn into or from the distal end of the central torque rod 608.

FIG. 6B illustrates the sheath 600 of FIG. 6A wherein the coil support 610 has been unwound and expanded diametrically, thus expanding the outer covering 606 at the distal end 604 to a diameter substantially similar to that of the proximal end 602. The lock 618 has been engaged to maintain relative position between the torque handle 616 and the sheath hub 614. In another embodiment, the function of the hub 618 can be replaced by a high friction or ratchet mechanism between the coil support 610 and the outer covering 606. In this latter embodiment, the central torque rod 608, the torque handle 616, and the engagement catch 612 can be removed from the sheath 600, by withdrawing proximally, to reveal a large central lumen in the outer covering 606, through which instrumentation (not shown) may be passed. The material of the coil support 610 is preferably spring-tempered metal such as, but not limited to, nitinol, titanium, stainless steel, Elgiloy, other cobalt-nickel alloys, and the like. The coil may be round or flat wire with a primary diametric dimension of 0.002 to 0.050 inches and preferably between 0.003 and 0.020 inches. The material of the torque rod 608 is the same as that for the coil support 610 or it may be a polymer such as PET, nylon, or the like. By counter-rotating the distal end of the coil support 610 relative to the proximal end, the coil support 610 can enlarge, or decrease, in diameter. An advantage of this embodiment is that the distal end 604 of the sheath 600 can be selectively dilated diametrically and then be recompressed prior to removal from the patient. A lubricant or slip layer may further be disposed between the coil support 610 and the outer covering 606. The outer covering 606 may be an elastomer like C-Flex, silastic, polyurethane, or the like, or it may be inelastic materials such as PET, polyethylene, or the like, which are furled or folded into a smaller diameter.

FIG. 7A illustrates a side view of an expandable sheath 700 comprising a proximal end 702 and a distal end 704. The sheath 700 further comprises an outer covering 706, a dilator shaft 708, a support frame 710, a dilatation balloon 712, a sheath hub 714, a dilator hub 716, a guidewire port 720, and a balloon inflation port 722. The distal end 704 has a reduced diameter relative to that of the proximal end 702.

Referring to FIG. 7A, the support frame 710 is a structure very similar to a stent such as that used for treating stenoses in the coronary arteries. The support frame 710 is embedded within, or resides interior to and against, the inner diameter of the outer covering 706. The support frame may be fabricated from stainless steel, titanium, martensitic nitinol, gold, platinum, tantalum, or other materials commonly used to fabricate cardiovascular stents. The support frame may be fabricated from wire, it may be laser cut from a tube or sheet of metal, or it may be photo-etched, mechanically machined, or machined using electron discharge methodology. The support frame, in an embodiment, is malleable and remains in the state to which it is dilated by the dilatation balloon 712. The support frame is preferably radiopaque under the circumstances in which it is used in vivo and may be fabricated from, alloyed with, or coated with materials such as gold, platinum, platinum iridium, or tantalum. The support frame wall thickness can range from 0.002 to 0.025 inches and preferably be between 0.003 and 0.012 inches. The support frame preferably comprises structures that permit flexibility. Such flexibility enhancing structures include disconnected "Z" or diamond-shaped ring segments, ring segments connected by a backbone or alternating backbone of wire, continuous undulating spirals, and the like. The outer covering is either unfurling, malleably expansible, or elastomeric. An exemplary expansible outer covering 706 comprises a low-density polyethylene disposed so that it embeds the stent. Another expansible outer covering 706 comprises a polyurethane, silastic or thermoplastic elastomer sleeve disposed around and frictionally covering the support frame 710. The outer covering 706 may further comprise an inner layer that is relatively low in sliding friction such as, but not limited to, high density polyethylene, FEP, PTFE, or the like. A furled outer covering 706 may be fabricated from stretch blow-molded PET. The outer covering 706 may be coated on its interior, exterior, or both, by silicone slip agents, hydrophilic hydrogels, or the like to minimize friction in passing the catheter through the body lumen as well as passage of instruments therein.

FIG. 7B illustrates the sheath 700 of FIG. 7A wherein the support frame 710 has become expanded by the dilatation balloon 712 having been pressurized by fluid injected into the inflation port 722 on the dilator hub 716 and transmitted to the balloon 712 through the dilator shaft 708. The support frame 710, at the distal end 704, has malleably expanded and holds the outer covering 706 in its radially expanded configuration.

Referring to FIG. 7B, the support frame 710 is affixed to the distal end of the proximal portion 702 of the sheath 700. The support frame 710 may be fully expanded at this proximal end even prior to expansion, as in FIG. 7A, and then neck down in the distal portion 704. Once expanded, the support frame 710 and the outer covering 706 have a generally continuous diameter and through lumen passing all the way from the proximal most portion of the sheath 700 to the distal end thereof. The outer covering 706 in the distal portion 704 will have stretched or unfurled to take on its larger diameter configuration. The recovery strength of the outer covering 706 is preferably such that it does not impart restorative forces greater than the resistive forces generated by the malleably expanded support frame 710. The distal region 704 remains dilated once the dilatation balloon 712, the dilator shaft 708, the dilator hub 716, and the inflation port 722 have been removed from the sheath 700. Thus, a large central lumen is generated within the sheath 700.

FIG. 8A illustrates a side view of an expandable sheath 800 comprising a proximal end 802 and a distal end 804. The sheath 800 further comprises a distal sheath covering 806, a proximal sheath covering 824, an obturator shaft 812, a distal shroud 810, a sheath hub 814, an obturator hub 816, and a guidewire port 818. The distal end 804 has a reduced diameter relative to that of the proximal end 802 because the distal sheath covering 806 has been folded or furled to form one or more longitudinal creases or pleats 820. The distal shroud 810 maintains the distal end 804 in its folded, small diameter configuration until it is removed by pushing it forward or pulling it backward. The transition region 822 connects the proximal sheath covering 824 and the distal sheath covering 806.

Referring to FIG. 8A, the distal sheath covering 806 begins at the transition region 822. The distal sheath covering 806 is thin-walled material that is folded into a plurality of pleats 820. The distal sheath covering 806 is fabricated from materials such as, but not limited to, PET, polyethylene, polypropylene, Hytrel, Pebax, polyimide, polyamide, HDPE, and the like. The wall thickness of the distal sheath covering 806 ranges from 0.001 to 0.020 inches. The distal sheath covering 806 may be heat set, or crosslinked by irradiation (e.g. gamma radiation or electron beam radiation), to sustain the pleats, creases, or folds 820. The distal sheath covering 806 is affixed to the distal end of the proximal sheath covering 824 by welding or adhesive bonding. The distal shroud 810 is permanently affixed to the exterior of the obturator shaft 812. The distal shroud 810 may be rigid or it may be flexible or elastomeric. The distal shroud 810 covers the distal sheath covering 806 and holds the distal end of said covering 806 compressed against the obturator shaft 812. The distal shroud 810 may be fabricated from C-Flex, polyurethane, silicone elastomer, and the like. The distal shroud 810 may be injection molded or cut from an extrusion or dip-coated structure. The distal shroud 810 may further comprise an inner spacer to prevent inadvertent withdrawal of the obturator and shroud until the shroud is advanced distally to release the sheath covering 806 so that it can expand. The inner spacer can further comprise, on its proximal end, a taper to facilitate proximal withdrawal into the sheath. The inner spacer may further comprise an undercut or relief on its distal end, which allows the shroud to maintain a low profile following eversion prior to withdrawal proximally. The obturator shaft 812 has a central through lumen, generally 0.020 to 0.050 inches in diameter that is operably connected to the guidewire port 818 on the obturator hub 816. The obturator shaft 812 is affixed to the obturator hub 816 by insert molding, welding, adhesive bonding, or the like. The obturator hub 816 is advanced forward causing the obturator shaft 812 to advance relative to the distal sheath covering 806. The shroud 810 pulls forward therewith and no longer surrounds the exterior of the sheath covering 806. The sheath covering 806 is now free to expand by unfurling the pleats 820 and serve as potential space for instrumentation once the obturator shaft 812 and its associated components are withdrawn from the sheath 800. In another embodiment, the shroud 810 is evertable and the obturator handle 816 is withdrawn proximally to simply pull the shroud 810 off the sheath covering 806 and out through the central lumen of the sheath 800. The shroud 810 may be fabricated from metals such as stainless steel or from polymers such as C-Flex, polypropylene, polyethylene, polyurethane, silicone elastomer, and the like. The proximal sheath covering 824 may be a unitary polymer tube fabricated from Hytrel, Pebax, polyethylene, FEP, PTFE, or the like. The proximal sheath covering 824 may further be a composite reinforced structure with an internal coil or braid reinforcement surrounded by polymers. The polymer on the interior may preferentially be a different polymer than that disposed on the exterior of the proximal sheath covering 824.

FIG. 8B illustrates a lateral cross section of the distal end 804 of the sheath 800 of FIG. 8A. In the illustrated embodiment, the distal sheath covering 806 has been folded to form four longitudinal creases, furls, or pleats 820. The obturator shaft 812 remains in place in the center of the sheath covering 806 and provides internal support to prevent buckling or kinking. When unconstrained, the sheath covering 806 is capable of expanding when a device is placed therethrough but there is no other support for the distal sheath covering 806, which is a relatively thin-wall un-reinforced structure.

Figure 9:
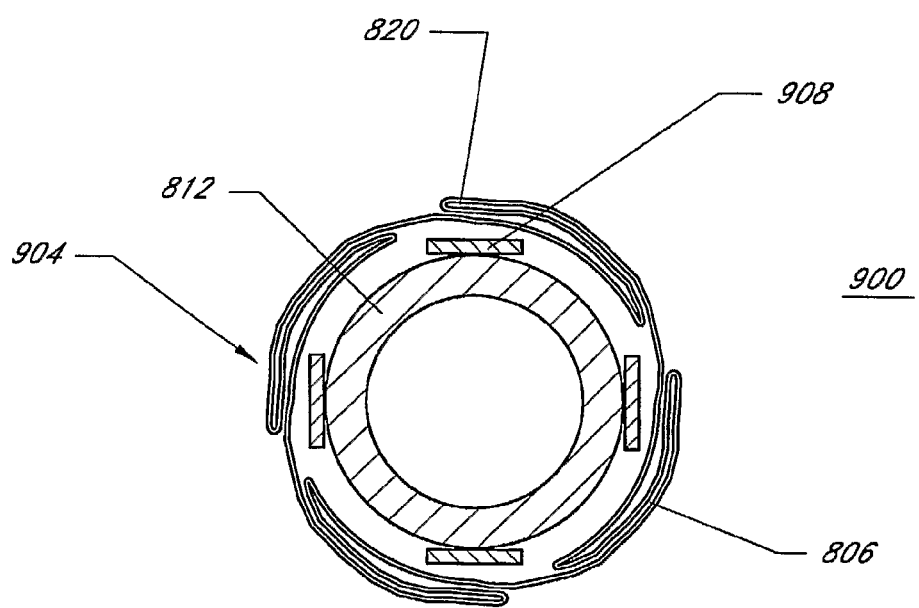
FIG. 9 illustrates a lateral cross-section of the distal end of a radially expandable transluminal sheath in its small diameter configuration, comprising thin wall unfurling sleeve over longitudinally disposed runners, through which instruments may be passed, according to an embodiment of the invention.

FIG. 9 illustrates a lateral cross-sectional view of the distal end 904 of another embodiment of the sheath 900. The sheath 900 is the same as the sheath 800 of FIG. 8A with the addition of runners 908 displaced within the sheath covering 806. The obturator shaft 812 is the same as the obturator shaft 812 of FIG. 8A. The runners 908 provide some column strength to prevent longitudinal collapse of the distal end 904, but also define a track through which instrumentation may be passed with minimal friction. The runners 908 expand freely in the radial direction when the pleats 820 unfold. The runners 908 may be affixed to the interior of the sheath covering 806 and further may be integral to or affixed to the non-expandable proximal portion of the sheath 900. The runners 908 may be affixed to the proximal sheath covering 824, referring to FIG. 8A, using adhesives, welding, or similar processes. The runners 908 may be extensions of the proximal sheath covering 824 that are slit to form circumferentially spaced-apart longitudinally disposed rods. The runners 908 may be integrally formed to the sheath covering 806 by being extruded or co-extruded into the sheath covering 806 when the latter is being fabricated. The runners 908 may be fabricated from metals such as stainless steel, titanium, cobalt nickel alloys, nitinol, or the like, or they may be fabricated from polymers such as but not limited to, polyethylene, polypropylene, PTFE, FEP, polyester, polyimide, polyamide, and the like.

Figure 10:
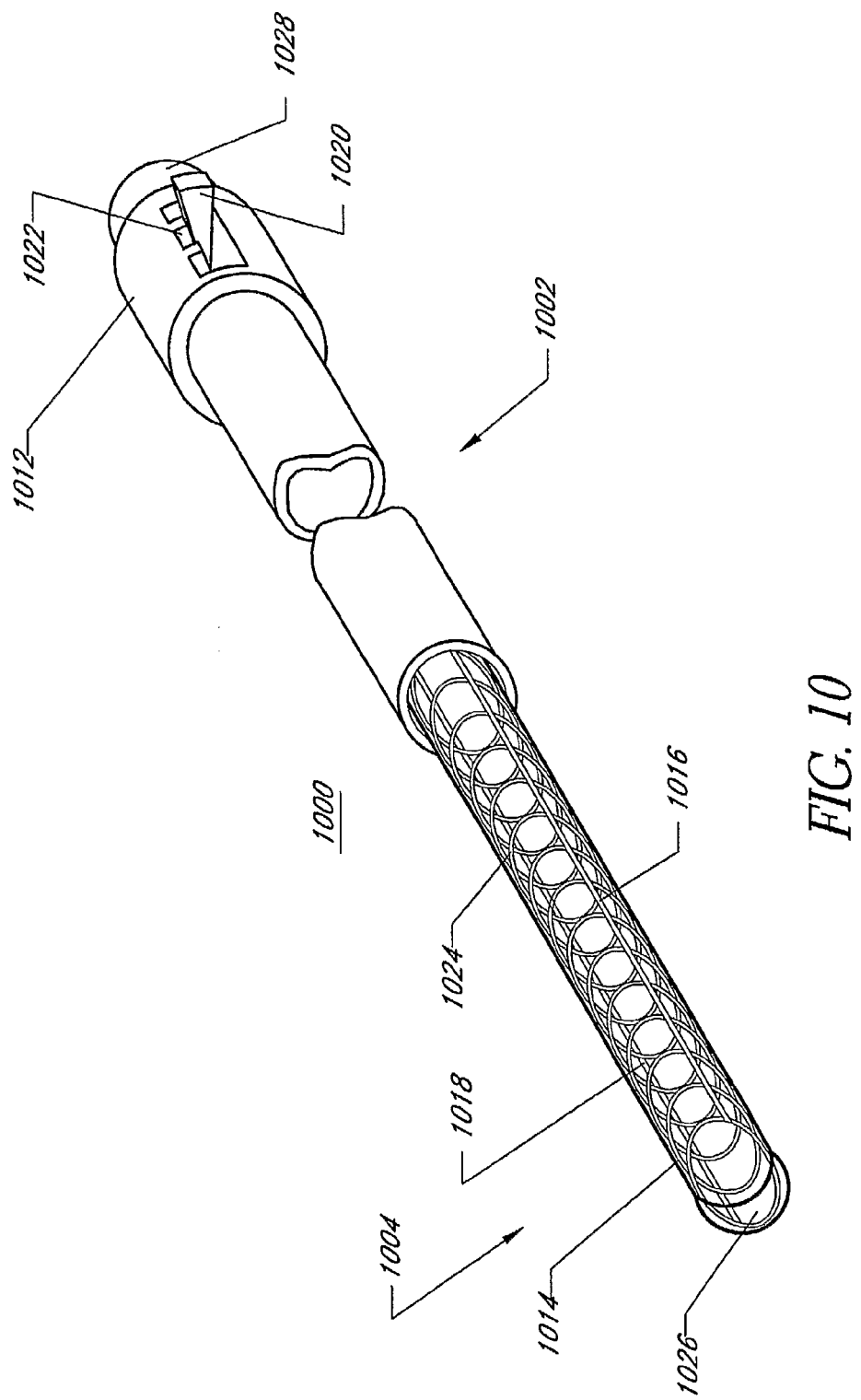
FIG. 10 illustrates a radially expandable transluminal sheath comprising hoop reinforcements that are rotated laterally to create a large diameter cross-section, and an exterior expandable sleeve, according to an embodiment of the invention.

FIG. 10 illustrates an oblique view of another embodiment of a sheath 1000. The sheath 1000 comprises a proximal end 1002 and a distal end 1004. The proximal end 1002 has a fixed diameter and is terminated, at its most proximal point, with a hub 1012. The hub 1012 further comprises a through port 1028, a control lever 1020, and a lock 1022. The distal end comprises an expandable sheath covering 1014, a plurality of rotating hoops 1024, a control rod 1018, and a stabilizer rod 1016. Axial movement of the control lever 1020 moves the control rod 1018 and swivels or rotates the rotating hoops 1024 about the stabilizer rod 1016 into a more or less perpendicular orientation, relative to the longitudinal axis of the sheath 1000. The lock 1022 maintains the position of the control lever 1020. The control lever 1020 is retracted proximally to rotate the hoops 1024 back into a substantially longitudinal orientation. The sheath covering 1014 is disposed external to the hoops 1024 and is forced to expand when the hoops rotate into the perpendicular plane. The sheath covering 1014 may be an unfurling non-distendable membrane or an elastomeric membrane. The sheath covering 1014 is preferably fluid impermeable. The control rod 1018 and the stabilizer rod 1016 are preferably flexible and allow for bending of the array of hoops 1024.

FIG. 11A illustrates a side cutaway view of an expandable transluminal sheath 1100 comprising a fixed diameter proximal end 1102 and a radially expandable distal end 1104. The sheath further comprises a proximal sheath outer layer 1124, a distal sheath outer layer 1106, a coil reinforcement 1116, a dilator shaft 318, a dilatation balloon 320, one or more longitudinal creases 1110 formed in the outer layer 1106, a sheath hub 308, and a dilator hub 316.

Referring to FIG. 11A, the distal sheath layer 1106 has incorporated therein a coil reinforcement 1116. The coil reinforcement 1116 is, in an embodiment, a wire fabricated from annealed metals such as, but not limited to, gold, stainless steel, titanium, tantalum, nickel titanium alloy, cobalt nickel alloys, and the like. The wire may be round wire or flat wire. Round wire diameters of 0.001 to 0.025 inches are appropriate for this embodiment, with preferable diameters in the range of 0.002 to 0.010 inches. Flat wires with widths of 0.005 to 0.040 inches and thickness ranging from 0.001 to 0.020 inches are suitable for this application. The wires of the coil reinforcement 1116 may be advantageously coated with materials that have increased radiopacity to allow for improved visibility under fluoroscopy or X-ray visualization. The radiopaque coatings for the coil reinforcement 1116 may be gold, platinum, tantalum, platinum iridium, and the like. The coatings may be imparted on the wire using vapor deposition processes, electroplating, dip coating, and the like. The coil reinforcement 1116 is preferably sandwiched between two layers of polymer, an inner and an outer layer. The inner layer may be a fluoropolymer such as fluorinated ethylene propylene, polytetrafluoroethylene, or the like. The inner layer may also be polyethylene, polyester, polyimide, polyamide, or other material that can be coated with lubricious coatings such as silicone oil or hydrophilic hydrogel. The outer layer may be fabricated from materials such as, but not limited to, polyethylene, Hytrel, PEBAX, polyurethane, C-Flex, or the like. The layers are preferably fused together with the coil sandwiched therebetween. Heat and pressure are applied to cause the fusing of the inner and outer layers. The wall is kept intentionally thin so that the entire distal tube structure comprising the coil reinforcement 1116 and the distal covering 1106 may be folded longitudinally to form flutes 1110. The mechanical strength of the coil maintains the shape without the need for external sleeves, although an external sleeve is a viable option. The strength of the distal polymer layer 1106 is not enough to overcome the forces generated by the coil reinforcement 1116. The external sleeve (not shown) can be either elastomeric or it may be a peel-away structure. Balloon dilatation occurs in the same way as that of the device in FIGS. 3A and 3B. The distal polymer layer 1106 at the distal end 1104 of the sheath 1100 may be the same as that of the layer 1124 at the proximal end 1102 of the sheath 1100. The exception is that the coil reinforcement in that area, if any, would be preferably spring temper. If the layers 1106 and 1124 are different, they are preferably fused together at their intersection.

FIG. 11B illustrates the sheath 1100 of FIG. 11A wherein the coil reinforcement 1116 and the distal outer layer 1106 have become expanded by the dilatation balloon 320 located on the distal end 1104. The coil reinforcement 1116, at the distal end 1104, has malleably unfolded and holds the outer covering 1106 in its radially expanded configuration. The crease line 1110 of FIG. 11A has been unfolded to permit full diameter opening of the sheath outer layer 1106. The dilator including the balloon 320, the dilator shaft 318, and the dilator hub 316 are next removed by withdrawing them proximally relative to the sheath 1100. The sheath 1100 is now able to form a path of substantially uniform internal size all the way from the proximal end to the distal end and to the exterior environment of the sheath 1100 at both ends. Through this path, instrumentation may be passed, material withdrawn from a patient, or both.

Figure 12:
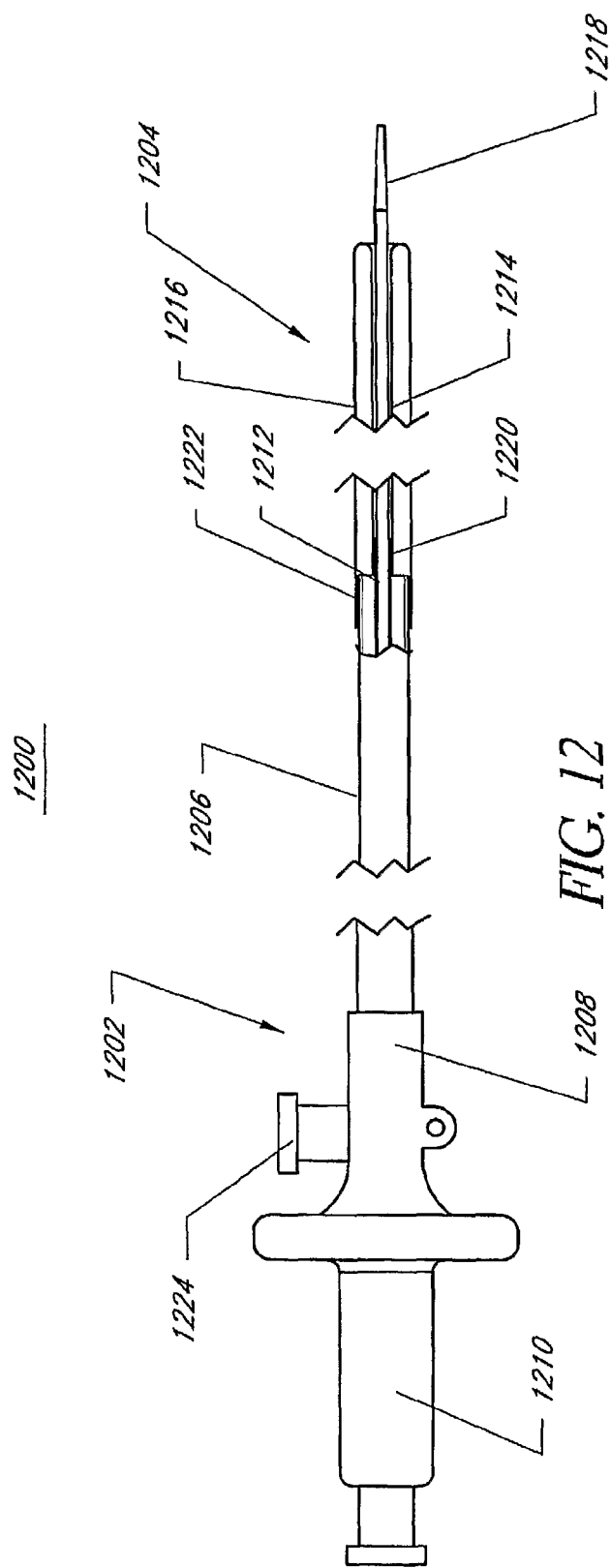
FIG. 12 illustrates a radially expandable transluminal sheath comprising a double wall and an internal annular inflation cavity that is pressurized to expand the sheath and provide some resistance against sheath wall collapse, according to an embodiment of the invention. The distal end of the sheath is shown in longitudinal cross-section.

FIG. 12 illustrates a radially expandable transluminal sheath 1200 comprising a proximal end 1202 and a distal end 1204. The proximal end 1202 comprises an outer tube 1206, an intermediate tube 1212, a sheath hub 1208, an inflation port 1224, and an obturator hub 1210. The distal end 1204 comprises a balloon inner layer 1214, a balloon outer layer 1216, the outer tube 1206, the intermediate tube 1212, the obturator shaft 1218, the inner balloon bond 1220, and the outer balloon bond 1222. Referring to FIG. 3A, the sheath 1200 may further comprise an optional tear away sleeve 310 and sleeve grip 312 to maintain the balloon inner layer 1214 and the balloon outer layer 1216, closely furled around the obturator shaft 1218.

Referring to FIG. 12, the inflation port 1224 is integral to the sheath hub 1208 and is operably connected to the annulus between the outer tube 1206 and the intermediate tube 1212, which opens into the interior of the annular balloon formed by the balloon outer layer 1216 and the balloon inner layer 1214. The balloon inner layer 1214 is bonded to the intermediate tube 1212 by the inner balloon bond 1220. The balloon outer layer 1216 is bonded to the outer tube 1206 by the outer balloon bond 1222. The balloon bonds 1220 and 1222 are either heat welds or adhesive welds, depending on the materials used for fabrication of the balloon 1214 and 1216 and the tubing. The balloon layers 1214 and 1216 are generally the same piece of material and are formed integrally, although they could be separate pieces alternatively fused together at the distal end. The balloon layers 1214 and 1216 may, one or both, be further reinforced with longitudinal strengthening members (not shown), similar to battens on a sailboat sail, that maintain column strength and prevent the balloon from compressing longitudinally when it is pressurized by fluid injected into the inflation port 1224. The battens are preferable to a tubular structure because they can dilate radially by separating but maintain longitudinal force. The sheath 1200 would have the advantage of being able to exert some modest pressure against tissue surrounding it and would still allow for instrument passage therethrough, as opposed to a sheath that had a collapsing potential space type of distal section. The obturator shaft 1218 and obturator hub 1210 are removed to permit passage of instruments through the sheath 1200. In yet another embodiment, the outer wall 1206 has a balloon inflation lumen (not shown) that would allow elimination of the intermediate tube 1212 and maximization of the through lumen of the sheath 1200.

Figure 13A:
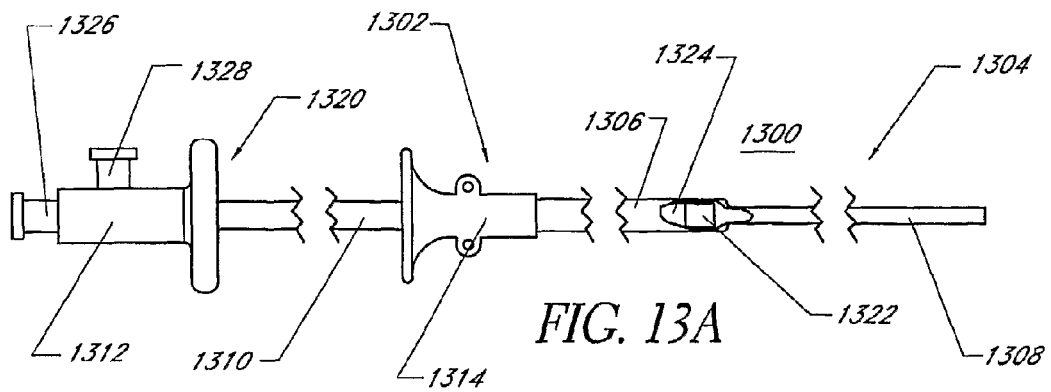
FIG. 13A illustrates a radially expandable transluminal sheath comprising an expandable distal outer wall, one or more wall reinforcements, and a hollow axially advanceable dilator, according to an embodiment of the invention.

FIG. 13A illustrates a side cutaway view of an expandable transluminal sheath 1300 comprising a fixed diameter proximal end 1302 and a radially expandable distal end 1304. The sheath further comprises a proximal outer layer 1306, a distal outer layer 1308, an outer layer transition zone 1324, and a sheath hub 1314. The sheath 1300 also comprises a translation dilator 1320 further comprising a dilator shaft 1310, a dilator hub 1312, and a dilator tip 1322. The dilator hub 1312 comprises an instrumentation port 1326 and an infusion port 1328.

Referring to FIG. 13A, the construction of the distal end 1304 comprises a distal outer layer 1308 that is either very thin walled and furled, or it is elastomeric and resilient. The thin walled and furled construction involves a distal outer layer 1308 that is approximately 0.0005 to 0.010 inches thick and preferably from 0.001 to 0.005 inches thick. The distal outer layer is fabricated from materials such as, but not limited to, polyethylene, polypropylene, polyurethane, polyvinyl chloride, Pebax, Hytrel, PET, FEP, PTFE, or the like. The distal outer layer 1308 is flexible and may be folded into longitudinal pleats that can be wrapped tightly circumferentially to create a small diameter axially elongate structure. The distal outer layer 1308 may further comprise flutes or runners integral to or affixed to the inner surface of the distal outer layer. The flutes or runners reduce friction between the distal outer layer 1308 and the dilator shaft 1310 as it is passed therethrough. They also may enhance folding and drainage. The distal outer layer 1308 may be further heat set, or radiation crosslinked, to cause it to be biased in the tightly wrapped furled configuration. The distal outer layer 1308 may comprise yet another layer exterior thereto, which is elastomeric and helps restore the distal outer layer 1308 to its small diameter configuration when the dilator shaft 1310 is retracted therefrom. The elastomeric layer may be fabricated from materials such as, but not limited to, C-flex, other thermoplastic elastomer, silicone elastomer, polyurethane, latex rubber, or the like. The elastomeric layer wall thickness is between 0.001 and 0.010 inches. The elastomeric layer may be affixed, using adhesives or welding, to the proximal tubing 1306 or it may be affixed to the distal end of the layer 1308, or both. The attachment of the elastomeric layer is preferably not complete circumferentially such that the attachment does not impede diametric expansion or contraction of the distal outer layer 1308. Radiopaque markers preferably delineate the proximal end and the distal end of the distal outer layer 1308, these radiopaque markers being able to move with the expanding and contracting sheath and not restricting its radial size change. The distal outer layer 1308 is able to bend through a radius as small as approximately 1 cm, or less, without kinking.

The proximal outer layer 1306 comprises construction elements that permit flexibility, kink resistance, column strength, thin walls, torqueability, lack of interior bumps or roughness, and lubricity. The proximal outer layer 1306 is affixed to the distal outer layer 1308 at the transition zone 1324, or the distal outer layer 1308 can be the continuation of the proximal layer 1306. The proximal end of the proximal outer layer 1306 is further permanently affixed to the distal end of the sheath hub 1314 so as not to obstruct the through lumen of the sheath 1300. The preferred construction of the proximal outer layer is a composite structure with a coil or braid of metal or high strength polymer surrounded by inner and outer layers of polymers that form the impermeable wall of the proximal outer layer 1306. The braid or coil is fabricated preferably from spring-temper metals such as, stainless steel, titanium, nitinol, or the like. The braid or coil may also be fabricated from polymers such as, but not limited to, PET, PEN, polyimide, polyamide, polyether-ether-ketone, or the like. The proximal outer layer 1306 is, in an embodiment, able to bend through a bend radius of 1 to 3 cm without kinking. The proximal outer layer 1306 walls are fabricated from materials such as, but not limited to, polyethylene, polypropylene, polyurethane, polyvinyl chloride, Pebax, Hytrel, PET, FEP, PTFE, or the like.

The translation dilator 1320 comprising the hub 1312, the shaft 1310, and the tip 1322 are flexible, kink resistant, possess column strength, torqueability and a through lumen with smooth walls free of roughness. The translation dilator 1320 has very thin walls, between 0.001 and 0.025 inches, so as to maximize the instrument carrying capacity of the system. The translation dilator is preferably fabricated from a coil or braid reinforced polymer and has construction similar to that of the proximal outer layer 1306 with the same materials applying to its construction. The tip 1322 is formed by radio frequency or induction heating or it is a separate piece of material welded or bonded to the distal end of the dilator shaft 1310. The tip 1322 is tapered on its exterior to facilitate passage through the diametrically compressed distal layer 1308. The tip 1322 is either hard or, in a preferred embodiment, soft and resilient. The translation dilator 1320, the proximal tube 1306, the distal tube 1308, all or any thereof may be coated with hydrophilic hydrogel or silicone oil to reduce friction and maximize pushability. The translation dilator is advanced distally by manual force on the dilator hub 1312 relative to the sheath hub 1314. In another embodiment, the translation dilator 1320 comprises an obturator (not shown) which projects beyond the distal end of the distal outer layer 1308 and facilitates introduction of the sheath 1300. The obturator may further comprise a guidewire lumen so that the sheath 1300 may be tracked over said guidewire into its target site.

Figure 13B:
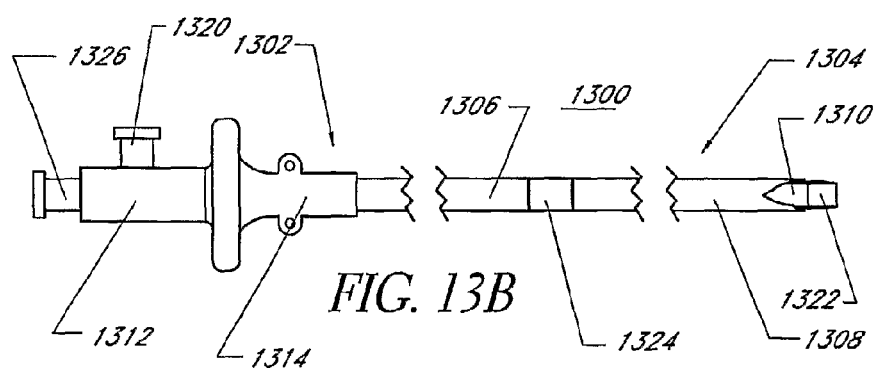
FIG. 13B illustrates the radially expandable transluminal sheath of FIG. 13A wherein the dilator has been translated or advanced forward to dilate the distal end of the sheath, according to an embodiment of the invention.

FIG. 13B illustrates the sheath 1300 of FIG. 13A wherein the outer layer 1306 has become expanded by the translation dilator 1320 which has been advanced distally to radially dilate the distal outer layer 1308. The distal outer layer 1308, has unfolded or elastically expanded and surrounds and is supported by the outer diameter of the hollow translation dilator 1320 to form its radially dilated configuration. The translation dilator 1320 further comprises an internal through lumen, accessed by the instrumentation port 1326, suitable for passage of instruments or the withdrawal or infusion of materials from (or into) the body. The translation dilator 1320 may be secured in its fully advanced position by engaging a lock or snap with the sheath hub 1314. Instrumentation passed through the sheath 1300 is passed through the instrumentation port 1326, which is operably connected to the through lumen of the dilator shaft 1310. Fluids may be injected or withdrawn through the fluid injection port 1328, which is operably connected to the through lumen in the dilator shaft 1310. The length of the sheath 1300, with the translation dilator 1320 fully advanced, is between 5 cm and 200 cm with a preferred length of between 25 and 75 cm.

Figure 13C:
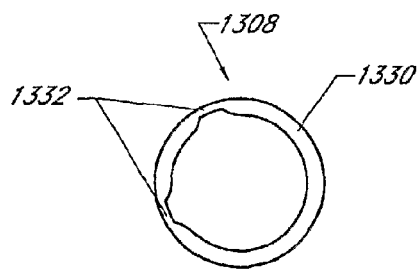
FIG. 13C illustrates a lateral cross-section of the distal portion of the transluminal sheath of FIG. 13A wherein the sheath covering comprises one or more longitudinally disposed thin areas of the wall, which are incorporated to facilitate folding of the sheath, according to an embodiment of the invention.

FIG. 13C illustrates a lateral cross-section of another embodiment of the distal tubing 1308. The distal tubing, in this embodiment, is extruded with thin areas 1332 and normal wall 1330. The illustrated embodiment shows two thin areas 1332 prior to folding. The spacing and magnitude of the thick and thin areas do not necessarily have to be uniformly placed or equally sized. The thin areas can be used to enhance the ability to form tight folds for diameter reduction.

Figure 13D:
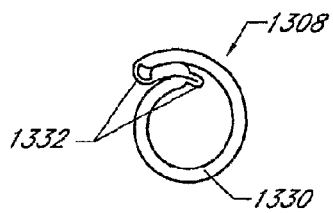
FIG. 13D illustrates the lateral cross-section with longitudinally disposed thin areas of FIG. 13C, which has been folded or creased, according to an embodiment of the invention.

FIG. 13D illustrates the distal tubing 1308 of FIG. 13C after it has been folded longitudinally. Other folds, including Napster™-type styles, star shapes, clover-leafs, and the like, are also possible. Such profiling would be performed on tubing fabricated from materials such as, but not limited to, polyethylene, PTFE, polyurethane, polyimide, polyamide, polypropylene, FEP, Pebax, Hytrel, and the like, at the time of extrusion. The liner would then be used, as-is, or it would be built up onto a mandrel with other layers as part of a composite tube. The composite tube can include coil, braid, or stent reinforcement. The thin areas 1332 facilitate tight folding of the layer 1308 and minimize the buildup of stresses and strains in the material that might prevent it from fully recovering to a round shape following unfolding. This type of sheath construction is suitable for the sheath embodiments shown in FIGS. 3, 4, 5, 11, 13, 15, 16, and 17.

FIG. 14A illustrates a side cutaway view of an expandable transluminal sheath 1400 comprising a fixed diameter proximal end 1402 and a radially expandable distal end 1404. The sheath 1400 further comprises a proximal outer layer 1406, a distal outer layer 1408, a self-expanding support structure 1410, and a sheath hub 1414. The sheath 1400 also comprises an optional releaseable sleeve or restraint (not shown), similar to that shown in FIG. 3A.

Referring to FIG. 14A, the self-expanding support structure 1410 underlies the distal outer layer 1408 or is embedded therein. Preferably, pockets exist in the distal outer layer 1408 to hold the self-expanding support structure 1410 so the transverse elements of the self-expanding support structure 1410 do not lock up on the outer layer 1408 when the elements are rotating or changing length during expansion, should the support structure 1410 be embedded within the outer layer 1408. The self-expanding support structure 1410 is fabricated similarly to a cardiovascular stent and comprises materials such as, but not limited to, superelastic nitinol, shape-memory nitinol, Elgiloy, titanium, stainless steel, and the like. The self-expanding support structure has element thicknesses of between 0.001 and 0.025 inches, and preferably between 0.002 and 0.015 inches. The configuration of the self-expanding support structure may include, but not be limited to, that of a serpentine spiral, a series of disconnected "Z" or diamond rings, a series of connected Z or diamond rings, brickwork slits, or the like. The distal outer layer 1408 is preferably a thin-wall unfurling structure or an elastomeric structure, both of which are similar to those appropriate for the distal tubing 1308 of FIGS. 13A and 13B. The proximal outer tubing 1406 is constructed similarly to that of the proximal tubing 1306 of FIGS. 13A and 13B.

FIG. 14B illustrates the sheath 1400 of FIG. 14A wherein the distal outer layer 1408 has become expanded by the self-expanding support structure 1410. The dilation of the support structure 1410 was initiated by the removal of the peel away sleeve or other restraint, or by phase change from martensitic to austenitic in the case of nitinol, either by exposure to body temperature or by Ohmic heating. The self-expanding support structure 1410 may further have dilated as a result of elevated temperature exposure in the body that caused shape-memory materials such as nitinol to assume austenitic phase. The distal outer layer 1408, has unfolded or elastically expanded and surrounds and is supported by the outer diameter of the self-expanding support structure 1410 to form its radially dilated configuration. The sheath 1400 in its expanded configuration further comprises an internal through lumen, suitable for passage of instruments or the withdrawal or infusion of materials from (or into) the body.

Figure 15A:
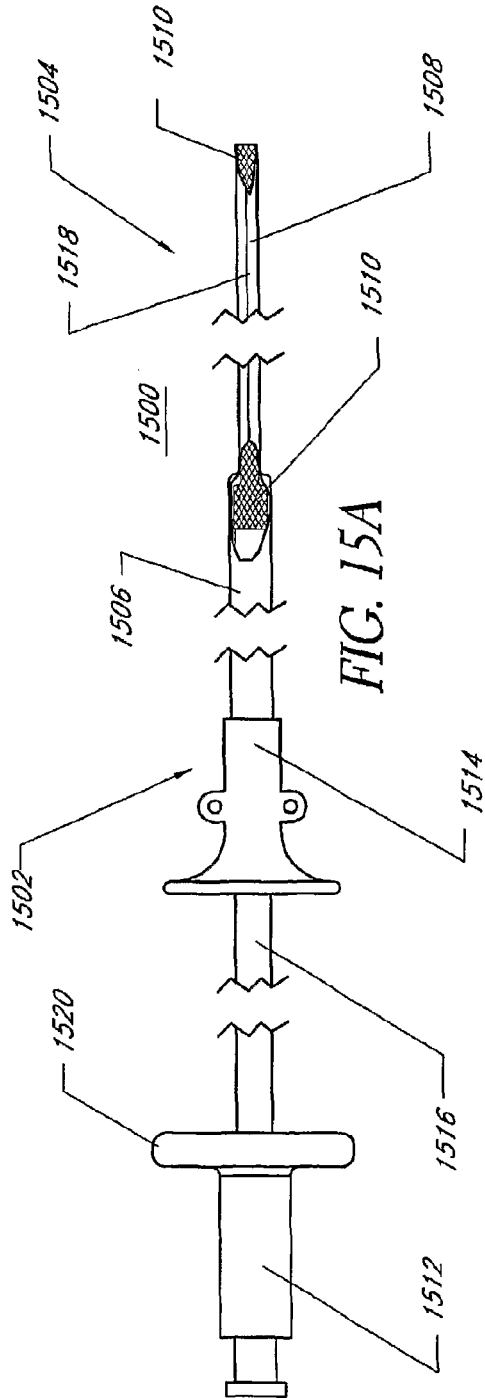
FIG. 15A illustrates a radially expandable transluminal sheath comprising an unfurling or elastomeric sleeve and an axially compressible braid at the distal end of the sheath, which is expanded axially and has a small diameter, according to an embodiment of the invention.

FIG. 15A illustrates a side cutaway view of an expandable transluminal sheath 1500 comprising a fixed diameter proximal end 1502 and a radially expandable distal end 1504. The sheath 1500 further comprises a proximal outer layer 1506, a distal outer layer 1508, a radially expanding braided support structure 1510, and a sheath hub 1514. The sheath 1500 further comprises a pusher tube 1516, a pusher hub 1512, a plurality of tensioning wires 1518, and a hub lock 1520.

Referring to FIG. 15A, the braid 1510 is affixed at the distal end to the distal end of the distal outer layer 1508. The distal outer layer 1508 is fabricated from a furled thin-walled polymeric material or an elastomeric material much the same as the sheath distal outer layer 1308 in FIGS. 13A and 13B. The crease or flute of the furled sheath 1518 is disposed longitudinally along the axis of the sheath 1500. The proximal end of the braid 1510 is affixed to the distal end of the pusher tube 1516. The pusher tube 1516 is affixed at its proximal end to the pusher hub 1512. The distal end 1504 of the sheath 1500 further comprises the plurality of tensioning wires 1518 which are affixed to the braided support structure 1510 at their distal end and affixed to the proximal outer layer 1506 at their proximal end. Axially distal movement of the pusher tube 1516 relative to the sheath hub 1514 causes the braided support structure 1510 to compress axially, thus expanding radially to is design diameter. Axially proximal movement of the pusher tube 1516 relative to the sheath hub 1514 causes the braid and surrounding distal sleeve to contract diametrically. The sheath 1500 may track through the lumen over a guidewire routed through its central lumen and it may further comprise an obturator within its inner lumen to aid in positioning.

Figure 15B:
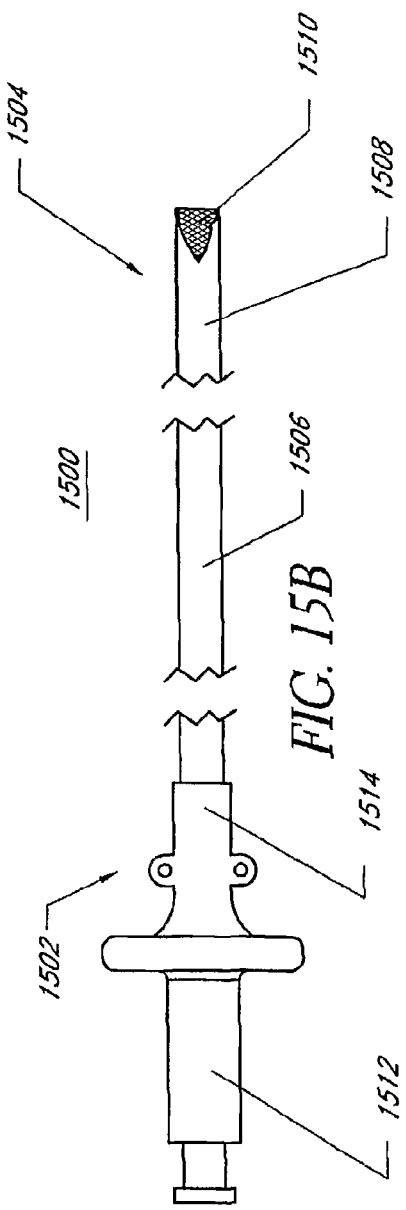
FIG. 15B illustrates the expandable sheath of FIG. 15A wherein the braid has been axially compressed forcing it and the distal end of the sheath to become larger in diameter, according to an embodiment of the invention.

FIG. 15B illustrates the sheath 1500 of FIG. 15A wherein the distal outer layer 1508 has become expanded by the advancing the pusher tube 1516 distally to compress the braid 1510 against the tension wires 1518. In another embodiment, the braid 1510 may have dilated as a result of elevated temperature exposure in the body that caused shape-memory materials such as nitinol, comprising the braid, to assume austenitic phase. The distal outer layer 1508, has unfolded or elastically expanded and surrounds and is supported by the outer diameter of the braid 1510 to form its radially dilated configuration. The sheath 1500 in its radially expanded configuration further comprises an internal through lumen suitable for passage of instruments or the withdrawal or infusion of materials from (or into) the body. The pusher hub 1512 may be temporarily, and reversibly affixed to the sheath hub 1514 by way of the hub lock 1520.

Figure 16A:
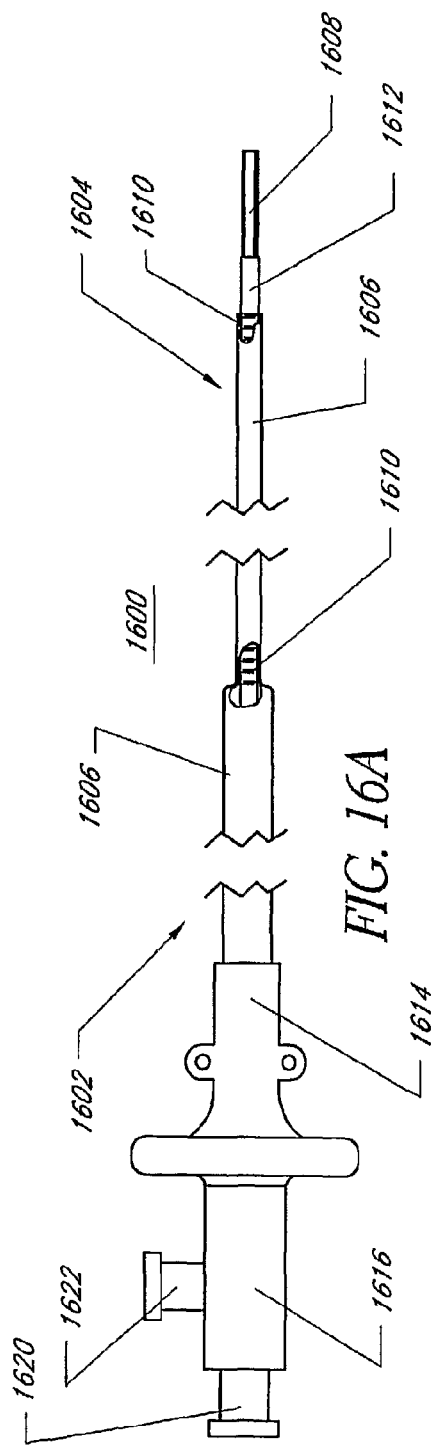
FIG. 16A illustrates a radially expandable transluminal sheath comprising an elastomeric, unfurling, or plastically deformable sleeve, a series of split ring reinforcements, and a balloon dilator, according to an embodiment of the invention.

FIG. 16A illustrates a side view of an expandable sheath 1600 comprising a proximal end 1602 and a distal end 1604. The sheath 1600 further comprises an outer covering 1606, a dilator shaft 1608, a split-ring support frame 1610, a dilatation balloon 1612, a sheath hub 1614, a dilator hub 1616, a guidewire port 1620, and a balloon inflation port 1622. The distal end 1604 has a reduced diameter relative to that of the proximal end 1602.

Referring to FIG. 16A, the split-ring support frame 1610 is a malleable structure that can be dilated by forces exerted by the inflated balloon 1612. The dilation is the same as that generated by the sheath 700 of FIGS. 7A and 7B. The split-ring support frame can be fabricated from wire or from flat sheets of metal or from tubes of metal. The preferred metal is selected from materials such as, but not limited to, titanium, tantalum, annealed stainless steels such as 316L, 304, and the like. The split ring support frame 1610 is disposed inside the inner diameter of the distal sheath tubing 1606. The split ring support frame 1610 has the advantage of being inexpensive to fabricate relative to other stent-like support designs. The split ring support frame 1610 can be configured as a series of ribs and a backbone, or as a series of staggered backbones to facilitate flexibility along more than one axis. Alternatively, in another embodiment, the split ring support frame 1610 can be self-expanding. The preferred configuration for the distal sleeve 1606 is a thin wall polymer that is furled into longitudinal flutes.

Figure 16B:
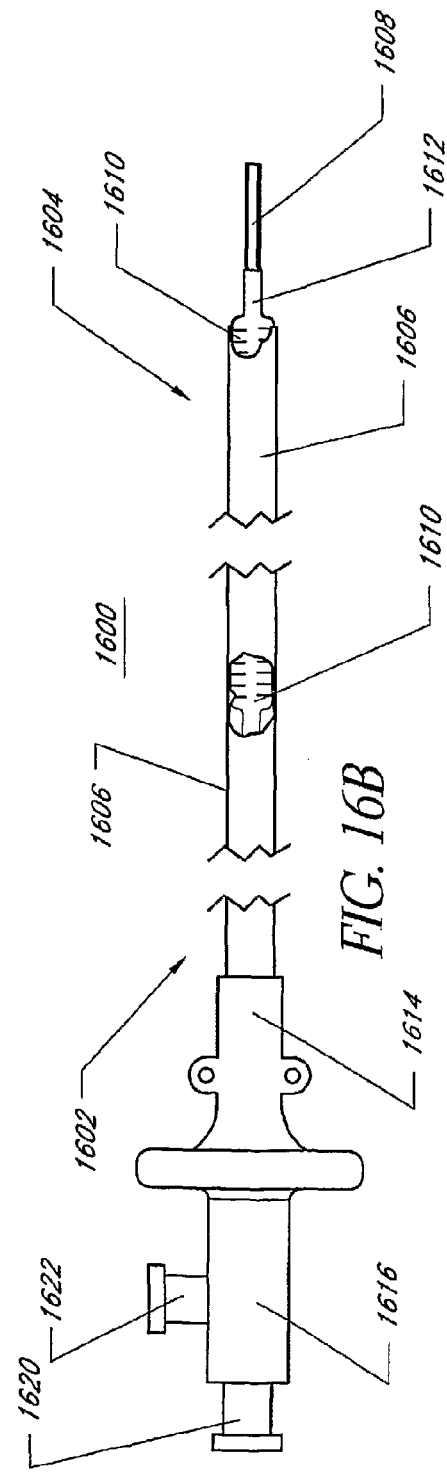
FIG. 16B illustrates the expandable sheath of FIG. 16A wherein the split rings have been expanded by the balloon dilator, according to an embodiment of the invention.

FIG. 16B illustrates the sheath 1600 of FIG. 16A wherein the support frame 1610 has become expanded by the dilatation balloon 1612 having been pressurized by fluid injected into the inflation port 1622 on the dilator hub 1616 and transmitted to the balloon 1612 through the annulus between the outer and inner tubes comprising the dilator shaft 1608. The split-ring support frame 1610, at the distal end 1604, has malleably expanded and holds the outer covering 1606 in its radially expanded configuration. The through lumen of the distal end 1604 is substantially similar to that of the proximal end 1602.

Figure 17A:
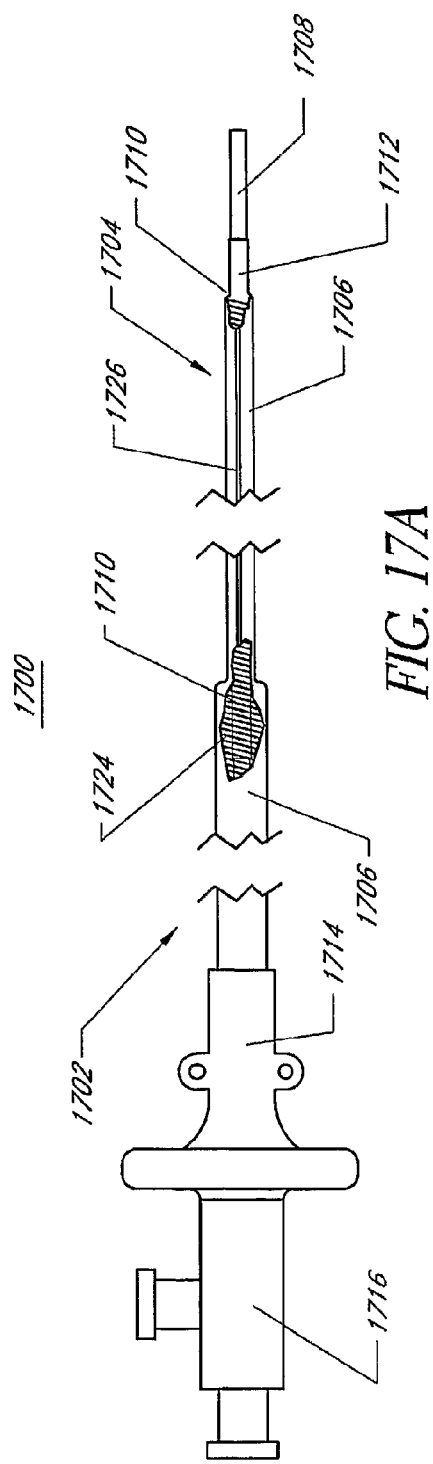
FIG. 17A illustrates a radially expandable transluminal sheath comprising a dilatation balloon, a malleable reinforced distal end and a spring coil or braid reinforced proximal end, the reinforcements coupled to an expandable sleeve, according to an embodiment of the invention.

FIG. 17A illustrates a side view of an expandable sheath 1700 comprising a proximal end 1702 and a distal end 1704. The sheath 1700 further comprises an outer covering 1706, a dilator shaft 1708, a malleable support coil 1710, a dilatation balloon 1712, a sheath hub 1714, a dilator hub 1716, a guidewire port 1720, a longitudinal crease 1726 in the distal outer covering 1706, and a balloon inflation port 1722. The distal end 1704 has a reduced diameter relative to that of the proximal end 1702. The proximal end of the sheath 1702 further comprises a spring temper reinforcing coil or braid 1724 to support the outer covering 1706.

Referring to FIG. 17A, the support coil for the proximal end 1702 is fabricated from spring-temper materials and is of constant diameter. The preferred spacing for the coils is roughly equivalent to the width of the wire to minimize any bumpiness on the interior of the sheath 1700. The wire winding is preferably flat wire to minimize bumpiness. Acceptable flat wire dimensions range in thickness from 0.001 to 0.025 inches and in width from 0.003 to 0.040 inches. The sheath cover 1706 preferably comprises some elasticity or malleability to maximize flexibility by stretching between the coil segments. The distal support 1710 is the same as that illustrated in FIGS. 11A and 11B and the distal sheath cover 1706 is also similar, although any of the distal segments disclosed in this document are suitable for use with this construction. Note that the pitch of the winding 1724 does not have to be the same as that for the winding 1710 because they have different functionality in the sheath 1700.

Figure 17B:
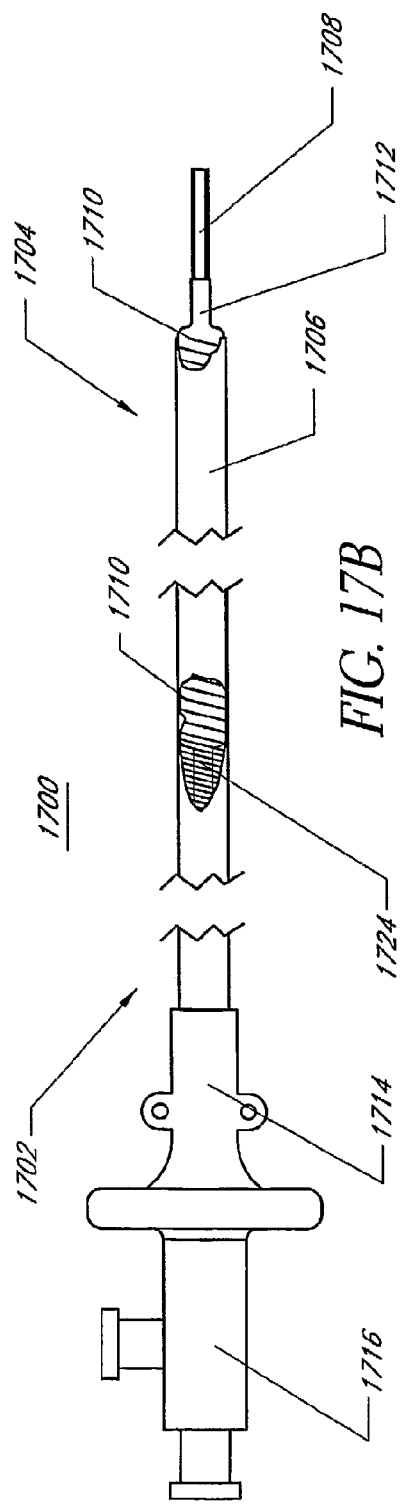
FIG. 17B illustrates the expandable sheath of FIG. 17A wherein the dilatation balloon has expanded the distal end of the sheath, according to an embodiment of the invention.

FIG. 17B illustrates the sheath 1700 of FIG. 17A wherein the malleable support coil 1710 has become expanded by the dilatation balloon 1712 having been pressurized by fluid injected into the inflation port 1722 on the dilator hub 1716 and transmitted to the balloon 1712 through the annulus between the outer and inner tubes comprising the dilator shaft 1708. The malleable support coil 1710, at the distal end 1704, has malleably expanded and holds the outer covering 1706 in its radially expanded configuration.

The present invention may be embodied in other specific forms without departing from its spirit or essential characteristics. For example, the sheath may include instruments affixed integrally to the interior central lumen of the mesh, rather than being separately inserted, for performing therapeutic or diagnostic functions. The hub may comprise tie downs or configuration changes to permit attachment the hub to the skin of the patient. The embodiments described herein further are suitable for fabricating very small diameter catheters, microcatheters, or sheaths suitable for cardiovascular or cerebrovascular access. These devices may have collapsed diameters less than 3 French (1 mm) and expanded diameters of 4 to 8 French. Larger devices with collapsed diameters of 16 French and expanded diameters of 60 French or larger are also possible. Such large devices may have orthopedic or spinal access applications, for example. Other devices of intermediate size, can have application in cardiovascular access using appropriate hemostatic valves and seals at the proximal end of the device. The described embodiments are to be considered in all respects only as illustrative and not restrictive. The scope of the invention is therefore indicated by the appended claims rather than the foregoing description. All changes that come within the meaning and range of equivalency of the claims are to be embraced within their scope.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or subcombinations of the specific features and aspects of the embodiments may be made and still fall within the scope of the invention. Accordingly, it should be understood that various features and aspects of the disclosed embodiments can be combine with or substituted for one another in order to form varying modes of the disclosed invention. Thus, it is intended that the scope of the present invention herein disclosed should not be limited by the particular disclosed embodiments described above, but should be determined only by a fair reading of the claims that follow.

What is claimed is:

1. A method of instrumenting a body lumen comprising the steps of:
    inserting a dilator into a sheath, said sheath having a radially collapsible distal end;
    collapsing the distal end of the sheath radially inward around the dilator such that the distal end of the sheath is smaller in diameter than the proximal end of the sheath;
    inserting the sheath and dilator into the body lumen transurethrally and advancing said sheath to a target treatment site of a bladder, ureter, or kidney;
    expanding the dilator, wherein the dilator expansion causes the distal end of the sheath to expand to a diameter substantially the same as that of the proximal end of the sheath;
    removing the dilator, wherein a central lumen remains that is substantially the same diameter moving from the proximal end to the distal end of the sheath; and
    introducing instruments or catheters through the central lumen of the sheath for a therapeutic or diagnostic procedure.

2. The method of claim 1 further comprising the step of removing the sheath from the body lumen, following completion of the procedure.

3. The method of claim 1 further comprising the step of introducing a guidewire into the body lumen prior to introducing the sheath into the body lumen.

4. The method of claim 3 further comprising the step of introducing the dilator and sheath over the guidewire, wherein the guidewire passes through a lumen in the dilator.

5. The method of claim 1 further comprising the step of collapsing the distal end of the sheath prior to removing the sheath from the body lumen.

* * * * *